United States Patent
Landi et al.

(10) Patent No.: US 10,408,844 B2
(45) Date of Patent: Sep. 10, 2019

(54) METHODS AND COMPOSITIONS IN DIAGNOSIS OF CHRONIC FATIGUE SYNDROME/MYALGIC ENCEPHALOMYELITIS

(71) Applicant: The Governors of the University of Alberta, Edmonton (CA)

(72) Inventors: Abdolamir Landi, Edmonton (CA); David Broadhurst, Edmonton (CA); D. Lorne J. Tyrrell, Edmonton (CA); Michael Houghton, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 0 days.

(21) Appl. No.: 15/543,943

(22) PCT Filed: Jan. 26, 2016

(86) PCT No.: PCT/CA2016/000022
§ 371 (c)(1),
(2) Date: Jul. 14, 2017

(87) PCT Pub. No.: WO2016/119044
PCT Pub. Date: Aug. 4, 2016

(65) Prior Publication Data
US 2018/0011110 A1  Jan. 11, 2018

Related U.S. Application Data

(60) Provisional application No. 62/108,978, filed on Jan. 28, 2015.

(51) Int. Cl.
| | |
|---|---|
| *G01N 33/68* | (2006.01) |
| *G01N 33/563* | (2006.01) |
| *G01N 33/58* | (2006.01) |
| *G01N 33/74* | (2006.01) |
| *G01N 33/96* | (2006.01) |
| *A61K 38/18* | (2006.01) |
| *A61K 38/19* | (2006.01) |
| *A61K 38/20* | (2006.01) |

(52) U.S. Cl.
CPC ..... *G01N 33/6869* (2013.01); *A61K 38/1866* (2013.01); *A61K 38/19* (2013.01); *A61K 38/2046* (2013.01); *A61K 38/2086* (2013.01); *G01N 33/563* (2013.01); *G01N 33/582* (2013.01); *G01N 33/6896* (2013.01); *G01N 33/74* (2013.01); *G01N 33/96* (2013.01); *G01N 33/6863* (2013.01); *G01N 2333/515* (2013.01); *G01N 2333/521* (2013.01); *G01N 2333/5418* (2013.01); *G01N 2333/5446* (2013.01)

(58) Field of Classification Search
None
See application file for complete search history.

(56) References Cited

U.S. PATENT DOCUMENTS

| | | |
|---|---|---|
| 2003/0100058 A1 | 5/2003 | Roschke et al. |
| 2006/0286586 A1 | 12/2006 | Drexhage et al. |
| 2012/0258883 A1 | 10/2012 | Chappell et al. |
| 2013/0309245 A1 | 11/2013 | Lombardi et al. |

FOREIGN PATENT DOCUMENTS

WO   2012106674   8/2012

OTHER PUBLICATIONS

Sturgill et al, Journal of Immunology Research, Mar. 2014; vol. 2014, pp. 1-5.*
Carruthers, Bruce M., et al., (2003) "Myalgic Encephalomyelitis/Chronic Fatigue Syndrome: Clinical Working Case Definition, Diagnostic and Treatment Protocols", Journal of Chronic Fatigue Syndrome, 11(1):7-36.
Khaiboullina, Svetlana F., et al. (2015) "Cytokine expression provides clues to the pathophysiology of Gulf War illness and myalgic encephalomyelitis", Cytokine, 72:1-8.
Stringer, Elizabeth Ann, et al., (2013) "Daily cytokine fluctuations, driven by leptin, are associated with fatigue severity in chronic fatigue syndrome: evidence of inflammatory pathology", Journal of Translational Medicine, 11(93):1-11.
Fletcher, et al., (2009) "Plasma cytoldnes in women with chronic fatigue syndrome". Journal of Translational Medicine, 7:96.
Brenu, E.W. et al., (2012) "Longitudinal investigation of natural killer cells and cytokines in chronic fatigue syndrome/myalgic encephalomyelitis". Journal of Translational Medicine, 10:88.
Smylie, A.L. et al., (2013) "A comparison of sex-specific immune signatures in Gulf War illness and chronic fatigue syndrome". BMC Immunology, 14:29.
Hardcastle, S.L. et al., (2015) "Serum immune proteins in moderate and severe chronic fatigue syndrome/myalgic encephalomyelitis patients". International Journal of Medical Sciences, 12(10): 764-772.

* cited by examiner

*Primary Examiner* — Bridget E Bunner
(74) *Attorney, Agent, or Firm* — Shweta Chandra; Bozicevic, Field & Francis LLP

(57) ABSTRACT

The present disclosure provides methods and compositions that find use in facilitating a diagnosis of chronic fatigue syndrome/myalgic encephalomyelitis (CFS/ME) in a subject. The methods and compositions involve measurement of at least one of proteins: IL-16, IL-7, VEGF, CXCL9, CX3CL1, CCL24, CCL19, and CCL11 in a body fluid sample of a subject suspected of having CFS/ME. Levels of one or more of the aforementioned proteins can be used to facilitate a diagnosis of a CFS/ME and/or confirm a diagnosis of CFS/ME. The methods and compositions of the present disclosure also find use in screening subjects for clinical trials and facilitating treatment decisions for a subject.

17 Claims, 12 Drawing Sheets

| Analyte | p-value | pFDR | median value (pg/ml) | | Up/Down in CFS | IntraCV | InterCV | Lower Limit of Detection | | Lower Limit of Quantification | |
|---|---|---|---|---|---|---|---|---|---|---|---|
| | | | CFS/ME | control | | | | Value (pg/ml) | % < LLOD | Value (pg/ml) | % < LLOQ |
| IL-16 | 9.38E-09 | 2.35E-07 | 403 | 767 | Down | 8% | 11% | 2 | 0% | 19 | 0% |
| IL-7 | 2.74E-04 | 0.002 | 10.9 | 12.6 | Down | 9% | 9% | 0.4 | 0% | 1.4 | 0% |
| CCL24 | 0.007 | 0.03 | 1530 | 1172 | Up | 6% | 8% | 2.4 | 0% | 24 | 0% |
| CXCL9 | 0.006 | 0.03 | 339 | 427 | Down | 9% | 18% | 0.4 | 0% | 4.8 | 0% |
| CX3CL1 | 0.01 | 0.04 | 3095 | 3482 | Down | 9% | 6% | 21.6 | 0% | 195.4 | 0% |
| VEGF | 0.01 | 0.05 | 88.4 | 107 | Down | 8% | 10% | 2.4 | 0% | 7.6 | 0% |
| CCL19 | 0.04 | 0.10 | 97 | 89.3 | Up | 8% | 5% | 0.2 | 0% | 4.8 | 0% |
| CCL11 | 0.05 | 0.11 | 714 | 646 | Up | 3% | 8% | 3.6 | 0% | 24.6 | 0% |
| IL-17 | 2.79E-05 | 3.49E-04 | 1.07 | 1.54 | Down | 24% | 19% | 2.2 | 84% | 2.4 | 87% |
| TNF-β | 0.003 | 0.02 | 0.1 | 0.13 | Down | 23% | 14% | 0.12 | 53% | 1.2 | 100% |
| IL-1β | 0.04 | 0.11 | 0.42 | 0.81 | Down | 23% | 7% | 0.2 | 27% | 1 | 64% |
| TNF-α | 0.06 | 0.12 | 3.42 | 4.03 | Down | 8% | 8% | 0.12 | 0% | 0.6 | 0% |
| CCL3 | 0.10 | 0.19 | 34.3 | 50.1 | Down | 5% | 10% | 4.8 | 0% | 18 | 12% |
| CCL17 | 0.14 | 0.25 | 105 | 116 | Down | 4% | 6% | 0.6 | 0% | 1.6 | 0% |
| CCL2 | 0.22 | 0.36 | 292 | 276 | Up | 6% | 9% | 0.2 | 0% | 0.6 | 0% |
| IFN-g | 0.27 | 0.42 | 5.45 | 6.46 | Down | 8% | 15% | 0.8 | 1% | 2.6 | 7% |
| IL-15 | 0.34 | 0.50 | 0.92 | 0.99 | Down | 12% | 9% | 0.4 | 2% | 1.4 | 91% |
| CCL26 | 0.44 | 0.58 | 275 | 272 | Up | 7% | 18% | 3.8 | 0% | 20.4 | 0% |

FIG. 1A

| Analyte | p-value | pFDR | median value (pg/ml) | | Up/Down in CFS | IntraCV | InterCV | Lower Limit of Detection | | Lower Limit of Quantification | |
| --- | --- | --- | --- | --- | --- | --- | --- | --- | --- | --- | --- |
| | | | CFS/ME | control | | | | Value (pg/ml) | % < LLOD | Value (pg/ml) | % < LLOQ |
| IL-6 | 0.43 | 0.60 | 1.15 | 1.37 | Down | 13% | 23% | 0.2 | 2% | 1.6 | 56% |
| IL-12/23p40 | 0.92 | 0.70 | 115 | 114 | Up | 6% | 12% | 0.6 | 0% | 1.4 | 0% |
| CCL22 | 0.98 | 0.70 | 1209 | 1217 | Down | 5% | 9% | 9 | 0% | 44.2 | 0% |
| IL-5 | 0.97 | 0.71 | 0.34 | 0.34 | Up | 36% | 10% | 0.8 | 92% | 6.2 | 100% |
| CCL13 | 0.91 | 0.71 | 354 | 377 | Down | 3% | 8% | 3.4 | 0% | 2.6 | 0% |
| IL-1α | 0.91 | 0.73 | 0.26 | 0.26 | Down | 23% | 10% | 10 | 99% | 0.6 | 86% |
| CCL4 | 0.89 | 0.74 | 181 | 199 | Down | 5% | 8% | 0.8 | 0% | 4.6 | 0% |
| GM-CSF | 0.84 | 0.75 | 0.21 | 0.24 | Up | 30% | 11% | 0.4 | 83% | 2 | 97% |
| IL-10 | 0.87 | 0.75 | 0.5 | 0.57 | Down | 19% | 19% | 0.08 | 0% | 0.6 | 56% |
| IL-4 | 0.82 | 0.76 | 0.11 | 0.08 | Down | 29% | 11% | 0.1 | 61% | 0.4 | 94% |
| IL-13 | 0.72 | 0.79 | 4.2 | 4.72 | Down | 26% | 9% | 1.8 | 22% | 4.2 | 50% |
| IL-2 | 0.80 | 0.80 | 0.32 | 0.33 | Down | 44% | 8% | 0.2 | 37% | 0.8 | 78% |
| CXCL10 | 0.70 | 0.80 | 283 | 289 | Down | 5% | 22% | 0.2 | 0% | 2.8 | 0% |
| IL-12p70 | 0.68 | 0.81 | 0.35 | 0.27 | Down | 32% | 9% | 0.4 | 63% | 3.4 | 99% |
| IL-8 | 0.79 | 0.83 | 331 | 374 | Down | 4% | 10% | 0.16 | 0% | 1.4 | 0% |
| β2M | 0.68 | 0.84 | 2.51 | 2.66 | Down | 9% | 15% | 0.02 | 7% | 0.04 | 7% |

| Clinical Diagnosis | Total # | IL-16 < 379 pg/ml | IL-7 < 9.9 pg/ml | VEGF < 74 pg/ml | CCL24 > 1836 pg/ml | CCL19 > 117 pg/ml | CXCL9 < 320 pg/ml | CX3CL1 < 2800 pg/ml |
|---|---|---|---|---|---|---|---|---|
| Controls | 79 | 13 | 16 | 17 | 18 | 18 | 18 | 18 |
| CFS | 100 | 45 | 41 | 40 | 41 | 34 | 44 | 38 |
| Sensitivity | | 45% | 41% | 40% | 41% | 34% | 44% | 38% |
| Specificity | | 84% | 80% | 78% | 77% | 77% | 77% | 77% |

FIG. 2B

| Clinical Diagnosis | Total # | IL-16 < 379 pg/ml and IL-7 < 9.9 pg/ml |
|---|---|---|
| Control | 79 | 2 |
| CFS | 100 | 25 |
| Sensitivity | | 25% |
| Specificity | | 98% |

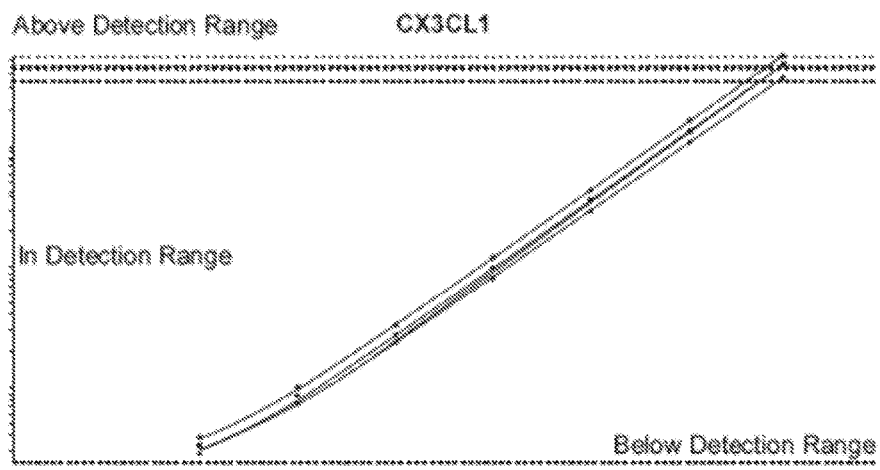
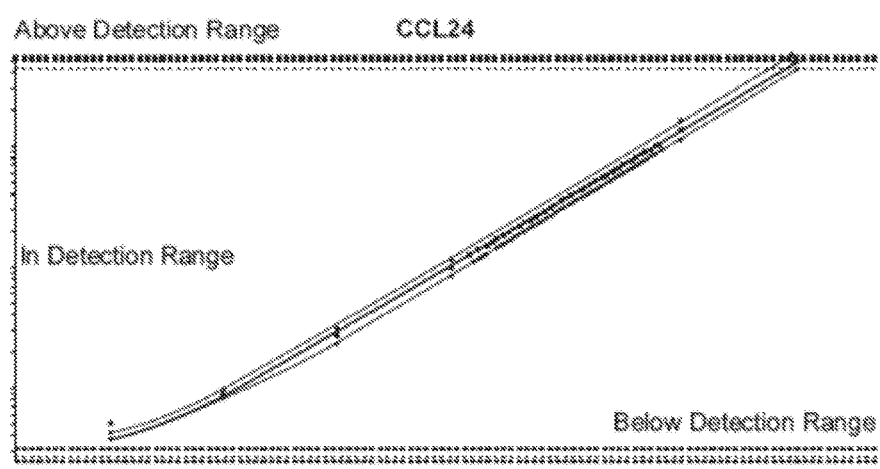
FIG. 4C

Logistic Regression Model Parameters and Significance Test.

| Analyte | Coefficient | S.E. | z | P>|z| | [95% Conf. Interval] | |
|---|---|---|---|---|---|---|
| IL-16 | -1.24 | 0.27 | -4.53 | 5.84E-06 | -1.78 | -0.70 |
| IL-7 | -0.92 | 0.45 | -2.04 | 0.041 | -1.80 | -0.04 |
| CCL24 | 0.89 | 0.29 | 3.02 | 0.002 | 0.31 | 1.47 |
| Constant | 3.98 | 2.56 | 1.56 | 0.12 | -1.04 | 9.01 |

FIG. 7

METHODS AND COMPOSITIONS IN DIAGNOSIS OF CHRONIC FATIGUE SYNDROME/MYALGIC ENCEPHALOMYELITIS

CROSS-REFERENCED TO RELATED APPLICATION

This application claims priority benefit of U.S. application Ser. No. 62/108,978, filed Jan. 28, 2015, which application in incorporated herein by reference in its entirety.

INTRODUCTION

Chronic fatigue syndrome or myalgic encephalomyelitis (CFS/ME) is a complex and severely debilitating disorder with unknown etiology and pathophysiology. It is characterized by profound fatigue, malaise, pain and cognitive dysfunction which lasts for more than six months and is not improved by bed rest and may be worsened by physical or mental activity. It is more common in young middle-age women with around 0.8-1.2 million people in the USA and 0.4-1% of the world population affected. In the USA alone, CFS/ME accounts for an annual seven billion Dollars in medical cost and twenty billion Dollars in lost work. The heterogeneous nature of the patient population results in a wide spectrum of affected individuals, who are often diagnosed with other conditions such as rheumatoid arthritis, autoimmune disease, and mental disorders. Diagnosis is also important for facilitating healthcare through insurance companies and social security. Currently, CFS/ME patients cannot readily access healthcare assistance and reimbursement.

SUMMARY

The present disclosure provides methods and compositions that find use in facilitating a diagnosis of CFS/ME in a subject. The methods and compositions involve measurement of at least one of analytes: IL-16, IL-7, VEGF, CXCL9, CX3CL1, CCL24, CCL19, and CCL11 in a body fluid sample of a subject suspected of having CFS/ME. Levels of one or more of the aforementioned proteins can be used to facilitate a diagnosis of a CFS/ME and/or confirm a diagnosis of CFS/ME. The methods and compositions of the present disclosure also find use in screening subjects for clinical trials and facilitating treatment decisions for a subject.

In certain embodiments, the methods and compositions involve measurement of level of interleukin-16 (IL-16) and at least one of IL-7, VEGF, CX3CL1, CXCL9, CCL24, CCL11, and CCL19, or combinations thereof. These levels can be used to facilitate a diagnosis of a CFS/ME and/or confirm a diagnosis of CFS/ME.

The methods of the present disclosure can include selecting a therapy for the subject based on the presence of CFS/ME. The methods of the present disclosure can include administering a therapy for the subject based on the presence of CFS/ME. Where the subject is undergoing therapy, the methods of the present disclosure can include modifying therapy for the subject based on the results of the diagnosis.

In certain embodiments, the method of facilitating diagnoses of chronic fatigue syndrome/myalgic encephalomyelitis (CFS/ME) in a subject suspected of having CFS/ME, may include measuring a level of IL-16 and a level of at least one of IL-7, VEGF, CCL24, CXCL9, CCL19, CX3CL1, and CCL11 in a body fluid sample of the subject; using the level of IL-16 and the level of at least one of IL-7, VEGF, CCL24, CXCL9, CCL19, CX3CL1, and CCL11 to determine presence of CFS/ME, where a decreased level of IL-16 and at least one of IL-7, VEGF, CX3CL1, and CXCL9 with reference to a threshold level of IL-16, IL-7, VEGF, CX3CL1, and CXCL9, respectively, are indicative of CFS/ME, or where a decreased level of IL-16 and an increased level of at least one of CCL24, CCL19, and CCL11 with reference to threshold level of IL-16, CCL24, CCL19, and CCL11, respectively, are indicative of CFS/ME.

In certain cases, the method may further include measuring level of IL-7 in the body fluid sample of the subject; and using the IL-7 level to determine presence of CFS/ME, wherein a decreased level of IL-7 with reference to threshold level is indicative of CFS/ME.

In certain cases, the method may further include measuring level of VEGF in the body fluid sample of the subject; and using the VEGF level to determine presence of CFS/ME, wherein a decreased level of VEGF with reference to a threshold level of VEGF is indicative of CFS/ME.

In certain cases, the method may further include measuring levels of IL-7 and VEGF in the body fluid sample of the subject, wherein decreased levels of IL-7 and VEGF compared to threshold levels are indicative of CFS/ME.

In certain cases, the method may further include measuring level of CCL24 in the body fluid sample of the subject; and using the CCL24 level to determine presence of CFS/ME, wherein an increased level of CCL24 with reference to a threshold level of CCL24 is indicative of CFS/ME.

In certain cases, the method may further include measuring levels of IL-7 and CCL24 in the body fluid sample of the subject; and using the IL-7 and CCL24 levels to determine presence of CFS/ME, wherein a decreased level of VEGF with reference to a threshold level of VEGF and an increased level of CCL24 with reference to a threshold level of CCL24 are indicative of CFS/ME.

In certain cases, the method may further include measuring levels of CXCL9 in the body fluid sample of the subject, wherein a decreased level of CXCL9 with reference to threshold level is indicative of CFS/ME.

In certain cases, the method may further include measuring level of CCL19 in the body fluid sample of the subject; and using the CCL19 level to determine presence of CFS/ME, wherein an increased level of CCL19 with reference to a threshold level of CCL19 is indicative of CFS/ME.

In certain cases, the method may further include measuring levels of CXCL9 and CCL19 in the body fluid sample of the subject; and using the CXCL9 and CCL19 levels to determine presence of CFS/ME, wherein a decreased level of CXCL9 with reference to threshold level of CXCL19 and an increased level of CCL19 with reference to a threshold level of CCL19 are indicative of CFS/ME.

In certain cases, the method may further include measuring levels of one or more of the aforementioned analytes and measuring level of CX3CL1 in the body fluid sample of the subject; and using the CX3CL1 level to determine presence of CFS/ME, wherein a decreased level of CX3CL1 with reference to a threshold level of CX3CL1 is indicative of CFS/ME.

In certain cases, the method may further include measuring levels of one or more of the aforementioned analytes and measuring level of CCL11 in the body fluid sample of the subject; and using the CCL11 level to determine presence of CFS/ME, wherein an increased level of CCL11 with reference to a threshold level of CCL11 is indicative of CFS/ME.

In certain cases, a method of facilitating diagnoses of chronic fatigue syndrome (CFS/ME) in a subject suspected of having CFS/ME may include measuring a level of IL-16 and levels of at least one of the following combinations of analytes: a) IL-7 and VEGF; b) IL-7 and CCL24; or c) CXCL9 and CCL19; using the level of the measured analytes to determine presence of CFS/ME, wherein decreased levels of IL-16, IL-7, and VEGF, or decreased levels of IL-16 and IL-7 and increased level of CCL24; or decreased levels of IL-16 and CXCL9 and increased level of CCL19, with reference to threshold levels is indicative of CFS/ME.

In certain cases, the method of facilitating a diagnosis of chronic fatigue syndrome (CFS/ME) in a subject suspected of having CFS/ME may include measuring levels IL-16, IL-7, and CCL24 in a plasma sample of the subject; assessing for presence of CFS/ME based on the measured levels, wherein decreased levels of at least one of IL-16 and IL-7 compared to threshold levels, and increased level of CCL24 compared to a threshold level is indicative of CFS/ME. In certain cases, the method may include calculating a score using the levels of IL-16, IL-7, and CCL24 and a formula:

$$score=3.98-1.24*\ln(IL\text{-}16)-0.92*\ln(IL\text{-}7)+0.89*\ln(CCL24)$$

The method may include diagnosing the subject as having CFS/ME when the score is above a threshold score or diagnosing the subject as not having CFS/ME when the score is at or below the threshold score.

Also provided herein are computers and computer systems that include a memory with instructions executed by a processor to perform the methods described herein for facilitating a diagnosis of CFS/ME.

Included herein are methods for treating a CFS/ME patient having an elevated level of one or more of the analytes: CCL24, CCL19, and CCL11 with an antagonist of the elevated analyte(s). Also provided herein are methods for treating a CFS/ME patient having a reduced level of one or more of the analytes: IL-16, CX3CL1, CCL24, CCL19, CCL11, IL-7, CXCL9, and VEGF by administering the analyte whose expression is decreased.

BRIEF DESCRIPTION OF THE DRAWINGS

FIGS. 1A and 1B depict results from analysis of the listed analytes.

FIG. 2A and FIG. 2B depict percent sensitivity and specificity of the listed analytes for CFS/ME.

FIGS. 4A-4C depict the consistent results for the standard curves for the indicated analytes from different experiments.

FIG. 7 depicts results from logistic regression model parameters and significance test.

DETAILED DESCRIPTION

Figure 3A:
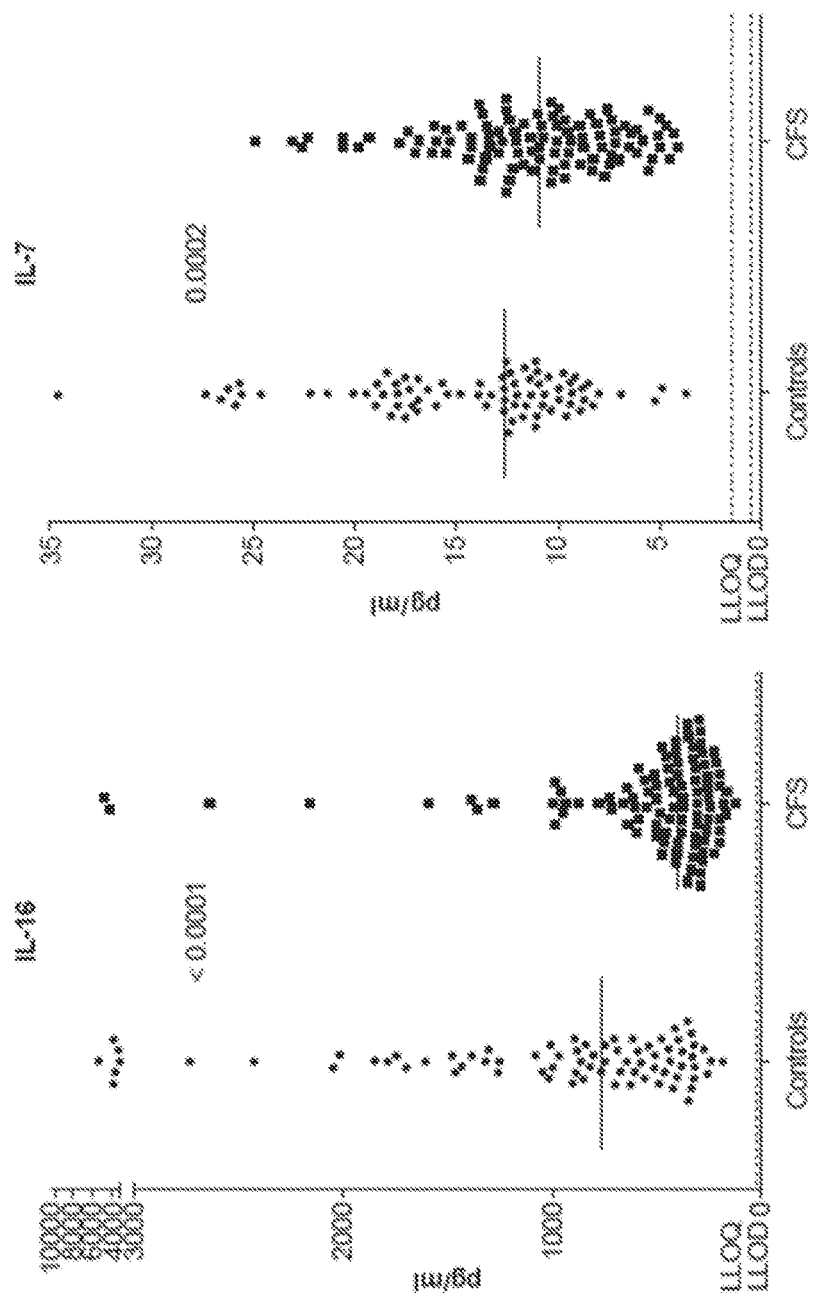
FIGS. 3A-3C provide analytes correlated to CFS/ME by univariate hypothesis testing after correction for age, sex and BMI.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a protein" includes a plurality of such proteins and reference to "the sample" includes reference to one or more samples and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "individual," "subject," and "patient," used interchangeably herein, refer to a human.

The term "healthy individual" in the context of the diagnostic methods of the present disclosure refers to an individual who is unaffected by a detectable illness, particularly CFS/ME. Healthy individuals include those who have not reported any complaint, symptom or sign of any diseases at the time of visit and, optionally, for the last month; have not had any history of fatigue, e.g., extreme fatigue, fatigue that worsens with physical or mental activity, and/or fatigue that does not improve with rest.

In the context of a polypeptide present in a biological sample, "polypeptide" refers to a naturally-occurring polypeptide present in an individual from whom the sample is obtained.

A "biomarker" or "marker" as used herein generally refers to an organic biomolecule (e.g., a polypeptide) which is differentially present in a sample taken from a subject of one phenotypic status (e.g., having a disease) as compared with a subject with another phenotypic status (e.g., not having the disease or having a different disease). A biomarker is differentially present between different phenotypic statuses if the mean or median level of the biomarker in a first phenotypic status relative to a second phenotypic status is calculated to represent statistically significant differences. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. As such, biomarkers can find use as markers for, for example, disease (diagnostics), therapeutic effectiveness of a drug (theranostics), and the like. Biomarkers are thus analytes in assays that facilitate diagnosis, theranostics, and the like. Biomarkers disclosed herein include IL-16, IL-7, VEGF, CX3CL1, CXCL9, CCL24, CCL11, and CCL19. These biomarkers are described herein as being present in a body fluid of a CFS/ME patient at a level different from the level of the biomarker in a normal or control subject.

A "biological fluid sample" or "body fluid sample" encompasses a variety of fluid sample types obtained from an individual. The definition encompasses blood (including blood fractions (e.g., serum, plasma)); and other liquid samples of biological origin (e.g., cerebrospinal fluid, saliva, urine, bile fluid). "Blood sample" refers to a biological sample, which is obtained from blood of a subject, and includes whole blood and blood fractions (e.g., plasma or serum) suitable for analysis in the present methods. In general, separation of cellular components and non-cellular components in a blood sample (e.g., by centrifugation) without coagulation provides a blood plasma sample, while such separation of coagulated (clotted) blood provides a blood serum sample. Examples of biological samples of blood include peripheral blood or samples derived from peripheral blood. The definition also includes samples that have been manipulated after their procurement, such as by treatment with reagents, solubilization, or enrichment for certain components, such as one or more polypeptides to be assayed. For example, a biological sample (e.g., blood) can be enriched for a fraction containing an analyte(s) of interest.

As used herein, the terms "determining", "assessing", "assaying", "measuring" and "detecting" refer to qualitative, quantitative and semi-quantitative determinations and as such, the term "determining" is used interchangeably herein with "assaying," "measuring," and the like.

"Sensitivity" refers to the fraction of people with the disease that a test correctly identifies as positive. "Specificity" refers to the fraction of people without the disease that the test correctly identifies as negative. The fractions with respect to sensitivity and/or specificity may be presented as a percentage. Where expressed as percentages, specificity can be calculated as by subtracting the sensitivity value for incorrect diagnosis from 100.

"Antibody" as used herein refers to an antigen-binding protein having one or more polypeptides that can be genetically encodable by immunoglobulin genes, or fragments of immunoglobulin genes, and which bind an antigen of interest. "Antibody" as used herein encompasses whole antibodies as well antigen-binding fragments of whole antibodies. Antigen-binding antibody fragments include, for example, Fab', (Fab')2, and the like. "Fab" as used herein refers to a minimal antigen-binding portion of an antibody that lacks an Fc portion (e.g., a heterodimer of a VH/VL pair of a tetrameric antibody). "(Fab')2" refers to Fab molecules that are covalently linked, usually covalently linked as found in nature, which lack an Fc portion. It should be noted that while various antibody fragments may be defined in terms of the digestion of an intact antibody, one of skill will appreciate that such fragments may be synthesized de novo either chemically or by utilizing recombinant DNA methodology.

Whole antibodies refers to antibodies composed of two pairs of polypeptides, where each pair includes one "light" chain polypeptide and one "heavy" chain polypeptide. The terms variable light chain (VL) and variable heavy chain (VH) refer to the portions of the light and heavy chains that contain the CDRs, respectively. Light chains can be classified according to their constant regions, which can be kappa or lambda. Heavy chains can be classified according to their constant regions, which can be gamma, mu, alpha, delta, or epsilon, which in turn define the immunoglobulin classes, IgG, IgM, IgA, IgD and IgE, respectively.

The term "antibody" encompasses polyclonal and monoclonal antibodies, and further encompasses antibodies of any class (e.g., IgM, IgG, and subclasses thereof). "Antibody" also encompasses hybrid antibodies, bispecific antibodies, heteroantibodies, chimeric antibodies, humanized antibodies, and functional fragments thereof which retain antigen binding. "Bispecific antibodies" may resemble single antibodies (or antibody fragments) but have two different antigen binding sites (variable regions). Heteroantibodies refers to two or more antibodies, or antibody binding fragments (e.g., Fab) linked together, each antibody or fragment having a different specificity. The antibodies may be conjugated to other moieties, and/or may be bound to a support (e.g., a solid support), such as a polystyrene plate or bead, test strip, and the like.

The phrase "specifically binds", when referring to a protein or a binding partner that binds a protein (e.g., an antibody that binds an antigen (e.g., analyte)), refers to a binding reaction between a protein and a binding partner (e.g., antibody and analyte) which is determinative of the presence of the protein in the presence of a heterogeneous population of proteins and other biologics. Thus, under designated conditions, a specified binding partner (e.g., antibody) binds preferentially to a particular protein and does not bind in a significant amount to other proteins present in the sample.

As used herein, the terms "determining", "assessing", "assaying", "measuring" and "detecting" refer to both quantitative and semi-quantitative determinations and as such, the term "determining" is used interchangeably herein with "assaying," "measuring," and the like. Where a quantitative determination is intended, the phrase "determining an amount" of an analyte and the like is used. Where either a quantitative and semi-quantitative determination is intended, the phrase "determining a level" of an analyte or "detecting" an analyte is used.

"Quantitative" assays in general provide information on the amount of an analyte in a sample. Quantitative assay may provide information on the concentration of an analyte relative to a reference (control), and are usually reported numerically, where a "zero" value can be assigned where the analyte is below the limit of detection. "Semi-quantitative" assays involve presentation of a numeric representation of the amount of the analyte in the specimen that is relative to a reference (e.g., a threshold, e.g., normal threshold or an abnormal threshold), where a "zero" value can be assigned where the analyte is below the limit of detection. In general, semi-quantitative results are compared against an accompanying reference interval to provide a qualitative interpretation of the result.

The terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease. The terms treatment or treating and the like encompass reduction in one or more symptoms of a disease. For example, treatment of CFS/ME encompasses reduction in one or more of symptoms of CFS/ME, e.g., a reduction in one or more of symptoms such as fatigue that is not improved by rest, fatigue worsened by physical activity, impairment in short-term memory or concentration, sore throat, tender lymph nodes, muscle pain, multi joint pain without swelling or redness, or headaches, and the like.

Methods of Facilitating a Diagnosis of Chronic Fatigue Syndrome

The present disclosure provides methods for facilitating a diagnosis of chronic fatigue syndrome (CFS/ME). Diagnosis can involve assessing whether the subject has CFS/ME so as to differentiate the subject from a healthy individual. Diagnosis can involve assessing whether the subject has CFS/ME so as to differentiate the subject from an individual who for example, feels fatigued or has a chronic disease that is accompanied with fatigue such as cancer, arthritis, muscular dystrophy, cachexia, sarcopenia, and the like. The present methods also involve confirming a clinical diagnosis of CFS/ME by measuring levels of the proteins disclosed herein.

The methods and compositions of the present disclosure also find use in facilitating treatment decisions for a subject. The methods and compositions of the present disclosure also find use in selecting individuals for a clinical trial for, e.g., assessing treatment of CFS/ME.

In certain embodiments, the method of facilitating diagnoses of chronic fatigue syndrome (CFS/ME) in a subject suspected of having CFS/ME may include a measuring level of at least one of the proteins: IL-16, CX3CL1, CCL24, CCL19, CCL11, IL-7, CXCL9, and VEGF in a body fluid sample of the subject; using the level of the measured protein to determine presence of CFS/ME, wherein a decreased level of one of the analytes: IL-16, IL-7, VEGF, CX3CL1, and CXCL9 with reference to a threshold level of IL-16, IL-7, VEGF, CX3CL1, and CXCL9, respectively, is indicative of presence of CFS/ME and wherein an increased level of one of the analytes: CCL24, CCL19, and CCL11 with reference to threshold level of CCL24, CCL19, and CCL11, respectively, is indicative of presence CFS/ME.

In certain cases, the method may include measuring a level of IL-16 in the body fluid sample of the subject; and using the IL-16 level to determine presence of CFS/ME, wherein a decreased level of IL-16 with reference to a threshold level of IL-16 is indicative of CFS/ME.

In certain cases, the method may include measuring a level of CX3CL1 in the body fluid sample of the subject; and using the CX3CL1 level to determine presence of CFS/ME, wherein a decreased level of CX3CL1 with reference to a threshold level of CX3CL1 is indicative of CFS/ME.

In certain cases, the method may include measuring a level of CCL24 in the body fluid sample of the subject; and using the CCL24 level to determine presence of CFS/ME, wherein an increased level of CCL24 with reference to a threshold level of CCL24 is indicative of CFS/ME.

In certain cases, the method may include measuring a level of CCL19 in the body fluid sample of the subject; and using the CCL19 level to determine presence of CFS/ME, wherein an increased level of CCL19 with reference to a threshold level of CCL19 is indicative of CFS/ME.

In certain cases, the method may include measuring a level of CCL11 in the body fluid sample of the subject; and using the CCL11 level to determine presence of CFS/ME, wherein an increased level of CCL11 with reference to a threshold level of CCL11 is indicative of CFS/ME.

In exemplary embodiments, two or more of the aforementioned biomarkers may be measured and their level utilized to facilitate a diagnosis of CFS/ME in a subject suspected of having CFS/ME. Using the measured level of one or more biomarker to determine presence of CFS/ME may include comparing the measured level of a biomarker to a threshold level of the biomarker and assessing the presence of CFS/ME in the subject when the measured level of the biomarker is below (e.g., when the measured biomarker is IL-16, IL-7, VEGF, CX3CL1, CXCL9) a threshold level for that biomarker or when the measured level of the biomarker is above (e.g., when the measured biomarker is CCL24, CCL19, or CCL11) a threshold level for that biomarker.

In exemplary embodiments, the method may include measuring a level of IL-16 and a level of at least one of IL-7, VEGF, CX3CL1, and CXCL9 in the body fluid sample to determine presence of CFS/ME, wherein a decreased IL-16 level and a decreased level of at least one of IL-7, VEGF, CX3CL1, and CXCL9 with reference to threshold levels is indicative of CFS/ME.

In certain cases, the method may include measuring levels of IL-16 and CXCL9 in the body fluid sample of the subject, wherein a decreased level of IL-16 and CXCL9 with reference to threshold levels is indicative of CFS/ME.

In certain cases, the IL-16 level in a body fluid sample of the subject may be below a threshold IL-16 level and the CXCL19 level may be at or above a threshold CXCL19 level. The subject may be determined to have CFS/ME if the level of at least one of the biomarkers such CCL19, CCL24 or CCL11 is increased with reference to threshold levels. For example, the subject may be diagnosed as having CFS/ME when the IL-16 level is below the IL-16 threshold level and CCL19 is above the CCL19 threshold level.

The method of facilitating a diagnosis of CFS/ME may include measuring level of IL-16 and the level of at least one of IL-7, VEGF, CX3CL1, and CXCL9 in the body fluid sample to determine presence of CFS/ME, wherein a decreased IL-16 level and a decreased level of at least one of IL-7, VEGF, CX3CL1, and CXCL9 with reference to threshold levels is indicative of CFS/ME.

In certain instances, levels of IL-16 and CXCL9 in the body fluid sample of the subject may be measured, wherein a decreased level of IL-16 and CXCL9 with reference to threshold levels is indicative of CFS/ME.

In another embodiment, the method may include measuring levels of IL-16, CXCL9 and CCL19 in the body fluid sample of the subject, wherein decreased levels of IL-16 and CXCL9 compared to threshold levels and increased level of CCL19 compared to a threshold level is indicative of CFS/ME.

In exemplary embodiments, the method may include measuring a level of IL-16 in a biological sample of a subject, particularly a subject suspected of having CFS/ME. In addition to detecting a level of IL-16, the methods optionally may include detecting a level of IL-7 and optionally VEGF. For example, the levels of IL-16, IL-7 and VEGF may be measured and when the levels of IL-16, IL-7 and VEGF are below the threshold levels, the subject may be diagnosed as having CFS/ME.

In certain cases, the methods may include measuring a level of IL-16 and at least one of CCL24, CCL11, and CCL19 in the body fluid sample of the subject, wherein a decreased level of IL-16 compared to threshold IL-16 level and an increased level of at least one of CCL24, CCL11, and CCL19 compared to threshold levels is indicative of CFS/ME. In certain instances, the method may include measuring levels of IL-16, IL-7, and CCL24, wherein decreased levels of IL-16 and IL-7 compared to threshold levels and increased level of CCL24 compared to a threshold level is indicative of CFS/ME.

In certain embodiments, a method of assessing presence of chronic fatigue syndrome (CFS/ME) in a subject suspected of having CFS/ME is provided. In certain cases, such an assessment may facilitate diagnosing CFS/ME in the subject. The method may include measuring level of one or more of IL-16, IL-7, VEGF, CX3CL1, CXCL9, CCL24, CCL19, and CCL11 in a body fluid sample of the subject. The subject may be assessed as having CFS/ME if level of one or more of IL-16, IL-7, VEGF, CX3CL1, and CXCL9 is decreased compared to threshold levels or if level of one or more of CCL24, CCL19, and CCL11 is increased compared to threshold levels.

In certain embodiments, the method may include measuring level of IL-16 and CXCL9 in a body fluid sample of a subject suspected of having CFS/ME and assessing the subject as having CFS/ME if level of IL-16 is decreased compared to threshold IL-16 level and level of CXCL9 is decreased compared to threshold CXCL9 level.

In certain embodiments, the method may include measuring level of IL16, CXCL9 and CCL19 in the body fluid sample of the subject and assessing that the subject has CFS/ME if level of IL-16 is decreased compared to threshold IL-16 level, level of CXCL9 is decreased compared to threshold CXCL9 level and level of CCL19 is increased compared to threshold CCL19 level. In certain embodiments, the subject may have decreased level of IL-16 and increased level of CXCL9, this subject may be diagnosed as having CFS/ME if CCL19 level is increased.

Exemplary embodiments disclose a method of diagnosing chronic fatigue syndrome (CFS/ME) in a subject. The method may include diagnosing the subject with CFS/ME when levels of at least one of IL-16, IL-7, VEGF, CX3CL1, and CXCL9 in a body fluid sample of the subject is decreased compared to a threshold level or when level of at least one of CCL24, CCL11, and CCL19 is increased compared to a threshold level.

In certain embodiments, the method may include diagnosing the subject with CFS/ME when levels of at least two of IL-16, IL-7, VEGF, CX3CL1, and CXCL9 is decreased compared to threshold levels and when levels of at least one of CCL24, CCL11, and CCL19 is increased compared to threshold levels.

In certain embodiments, the method may include assessing that there is an increased likelihood that the subject has CFS/ME when levels of at least three of IL-16, IL-7, VEGF, CX3CL1, and CXCL9 are decreased compared to threshold levels. Exemplary methods include diagnosing the subject with CFS/ME when levels of IL-16, IL-7 and VEGF are decreased compared to threshold levels; or when levels of IL-16 and IL-7 are decreased and when levels of CCL24 is increased compared to threshold levels; or when levels of IL-16 and CXCL9 are decreased and when levels of CCL19 is increased compared to threshold levels.

As used herein, the phrase "normal level" refers to the level of a biomarker (e.g., a polypeptide, such as a cytokine/chemokine disclosed herein) present in a body fluid of a healthy individual or an individual who does not have and is not suspected of having CFS/ME. Normal level may vary between different body fluids and in the context of comparison to level in a body fluid sample of a subject, the comparison is with normal level present in the same body fluid. For example, plasma level of a cytokine in a subject is compared to normal plasma level of the cytokine.

As used herein, a decreased or increased level compared to a normal level refers to a significant change in level compared to a normal level. A significant change may be a change of at least about 15% or more, such as 15%, 20%, 25%, 30%, 35% or more. For example, a decreased level of IL-16 in a plasma sample of a subject compared to normal IL-16 plasma level is a decrease of 15% or more. Similarly, an increased level of CCL19 in a plasma sample of a subject compared to normal CCL19 plasma level is an increase of 15% or more.

The phrase, "threshold level" in the context of a biomarker for CFS/ME as disclosed herein refers to a biomarker level that can be used to distinguish between individuals who do not have CFS/ME and individuals who have CFS/ME such that a biomarker level in a sample that is below a threshold level of that biomarker indicates an increased likelihood of CFS/ME in the individual. Similarly, level of another biomarker may be above a threshold level of that biomarker, may then be indicative of CFS/ME. Thus, a "biomarker threshold value" refers to an assay value (e.g., amount of a biomarker), which is an approximate value that distinguishes the likelihood that a disease is present in the individual tested from the likelihood that a disease is not present in the individual tested, with a pre-selected specificity and/or sensitivity.

For example, a biomarker threshold value can represent an approximate level of a biomarker that detects affected subjects at a desired sensitivity (e.g., at least 34%, at least 38%, at least 40%, at least 41%, at least 44%, at least 45%, at least 50%, at least 55%, at least about 60%, at least 70%, or at least 80% sensitivity or more).

It will be appreciated that the precise number value for threshold values can vary with the type of assay and reagents used to detect the biomarkers. For example, the assay values upon which the threshold values for IL-16, IL-7, VEGF described herein are based on assay values obtained using plasma samples and a multiplex ELISA kit from Meso Scale Discovery Company. However, regardless of the assay and reagents used, the correlations between a threshold value of a biomarker and likelihood of a disease state will be present regardless of the assays and reagents used. Thus, so long as the test samples are assayed for the biomarker (e.g., IL-16, IL-7, VEGF) using an assay platform and reagents of the same general type (e.g., polypeptide assay) and, generally preferably, same sensitivity as the assay platform and reagents used to determine the threshold values of the biomarker (IL-16, IL-7, VEGF, respectively), the findings upon which the methods of the present disclosure are based will be preserved.

In embodiments where a level of a biomarker in a body fluid sample of a subject is compared to a normal level or a threshold level, the measured level and the threshold level of that biomarker may be in the context of the same body fluid. Further, comparison of level of a first, second, third, or more biomarker to threshold levels or normal levels refers to comparison of level of a first biomarker to threshold level of that first biomarker, the comparison of level of a second biomarker to threshold level of that second biomarker, comparison of level of a third biomarker to threshold level of that third biomarker and so on. For example, decreased levels of IL-16, IL-7, VEGF, CX3CL1, and CXCL9 compared to threshold levels, refers to comparison of the of level of IL-16, IL-7, VEGF, CX3CL1, and CXCL9 to the threshold level of IL-16, IL-7, VEGF, CX3CL1, and CXCL9, respectively. Thus, when levels of IL-16, IL-7, CX3CL1 are compared to threshold levels, the level of IL-16 is compared to IL-16 threshold level, the level of IL-7 is compared to IL-7 threshold level, the level of CX3CL1 is compared to CX3CL1 threshold level, and so on.

Values of threshold levels of the biomarkers provided herein can be determined as described herein, e.g., by assaying level of a biomarker in control populations, and, through application of statistical analysis, identifying level of the biomarker that is present in at least 45%, at least 50%, at least 55%, at least about 60%, at least 70%, at least 80%, or at least 90% or more of patients having CFS/ME.

In addition to the methods described above, the present disclosure also provides the following combination of biomarkers, which find use in facilitating/confirming a diagnosis of CFS/ME with a high specificity. In certain embodiments, the measuring of levels of the following combination of markers may be used to diagnose a subject as having CFS/ME:

i) IL16, IL-7 and VEGF;
ii) IL16, IL-7 and CCL24; or
iii) IL-16, CXCL9 and CCL19

In certain cases, the method may include measuring plasma levels of IL-16, CCL24, and IL-7 and calculating a score using the plasma levels of IL-16, CCL24, and IL-7 and a formula:

$$score = 3.98 - 1.24 \times \ln(IL\text{-}16) - 0.92 \times \ln(IL\text{-}7) + 0.89 \times \ln(CCL24)$$

In certain cases, the method may include diagnosing the subject with CFS/ME when the score is above a threshold or diagnosing the subject as not having CFS/ME when the score is at or below the threshold. In certain cases, the threshold may be about 0.77. In certain cases, the body fluid sample may be plasma sample and the threshold may be 0.77.

A method for determining whether a subject has chronic fatigue syndrome (CFS/ME) is also provided. The method may include determining level of at least one of IL-16, IL-7, VEGF, CXCL9 and CX3CL1; and at least one of CCL11, CCL19 and CCL24 in a body fluid sample of the subject; comparing the measured levels to threshold levels, wherein a decreased level of at least one of IL-16, IL-7, VEGF, CXCL9 and CX3CL1 and an increased level of at least one of CCL11, CCL19 and CCL24 may be indicative of CFS/ME.

In certain cases, a decreased level of at least two of IL-16, IL-7, VEGF, CXCL9 and CX3CL1 and an increased level of at least one of CCL11, CCL19 and CCL24 may be indicative of CFS/ME.

In certain cases, a decreased level of at least three of IL-16, IL-7, VEGF, CXCL9 and CX3CL1 is indicative of CFS/ME.

In certain cases, a decreased level of at least two of IL-16, IL-7, VEGF, CXCL9 and CX3CL1 and an increased level of at least one of CCL11, CCL19 and CCL24 may be indicative of CFS/ME.

In certain cases, a decreased level of IL-16, IL-7, and VEGF may be indicative of CFS/ME. In certain embodiments, a decreased level of IL-16 and IL-7 and increased level of CCL24 may be indicative of CFS/ME. In certain embodiments, a decreased level of IL-16 and CXCL9 and increased level of CCL19 may be indicative of CFS/ME.

In certain cases, the body fluid sample may be a plasma sample and the threshold level of IL-16 may be about 379 pg/ml. A subject may be diagnosed as having CFS/ME if the level of IL-16 in a plasma sample of the individual is less than about 350-390 pg/ml for example, less than about 355-385 pg/ml, less than about 360-380 pg/ml, or less than about 365-375 pg/ml.

In certain cases, the body fluid sample may be a plasma sample and the threshold level of IL-7 may be about 9.9 pg/ml. A subject may be diagnosed as having CFS/ME if the level of IL-7 in a plasma sample of the individual is less than about 7-12 pg/ml for example, less than about 7.5-11.5 pg/ml, less than about 8-11 pg/ml, less than about 8.5-10.5 pg/ml, or less than about 9-10 pg/ml.

In certain cases, the method may include measuring level of VEGF in a body fluid sample of the subject and determining that the subject has CFS/ME when level of VEGF is decreased compared to a threshold VEGF level. In certain cases, the body fluid sample may be a plasma sample and the threshold VEGF may be about 74 pg/ml. A subject may be diagnosed as having CFS/ME if the level of VEGF in a plasma sample of the individual is less than about 65-85 pg/ml for example, less than about 70-80 pg/ml, or less than about 75-80 pg/ml.

In certain cases, the method may include measuring level of CXCL9 in a body fluid sample of the subject and determining that the subject has CFS/ME when level of CXCL9 is decreased compared to a threshold CXCL9 level. In certain cases, the body fluid sample may be a plasma sample and the threshold CXCL9 may be about 320 pg/ml. A subject may be diagnosed as having CFS/ME if the level of CXCL9 in a plasma sample of the individual is less than about 300-350 pg/ml for example, less than about 305-345 pg/ml, less than about 310-340 pg/ml, less than about 315-340 pg/ml, less than about 315-335 pg/ml, or less than about 315-330 pg/ml.

In certain cases, the method may include measuring level of CX3CL1 in a body fluid sample of the subject and determining that the subject has CFS/ME when level of CX3CL1 is decreased compared to a threshold CX3CL1 level. In certain cases, the body fluid sample may be a plasma sample and the threshold CX3CL1 may be about 2800 pg/ml. A subject may be diagnosed as having CFS/ME if the level of CX3CL1 in a plasma sample of the individual is less than about 2500-3000 pg/ml for example, less than about 2600-2900 pg/ml, less than about 2700-2850 pg/ml, or less than about 2750-2850 pg/ml.

In certain cases, the method may include measuring level of CCL24 in a body fluid sample of the subject and determining that the subject has CFS/ME when level of CCL24 is increased compared to a threshold CCL24 level. In certain cases, the body fluid sample may be a plasma sample and the threshold CCL24 may be about 1836 pg/ml. A subject may be diagnosed as having CFS/ME if the level of CCL24 in a plasma sample of the individual is more than about 1500-2000 pg/ml for example, less than about 1600-1950 pg/ml, less than about 1650-1900 pg/ml, or less than about 1700-1950 pg/ml.

In certain cases, the method may include measuring level of CCL19 in a body fluid sample of the subject and determining that the subject has CFS/ME when level of CCL19 is increased compared to a threshold CCL19 level. In certain cases, the body fluid sample may be a plasma sample and the threshold CCL19 may be about 117 pg/ml. A subject may be diagnosed as having CFS/ME if the level of CCL19 in a plasma sample of the individual is more than about 100-150 pg/ml for example, less than about 105-145 pg/ml, less than about 110-140 pg/ml, less than about 115-135 pg/ml, less than about 110-130 pg/ml, or less than about 110-120 pg/ml.

In certain cases, a multi-analyte analysis may be performed to determine likelihood of a subject having CFS/ME. In this embodiment, the threshold level of IL-16 may be set higher than 350-390 pg/ml. For example, the threshold level of IL-16 may be about 500-530 pg/ml. In exemplary cases, when the IL-16 level of an individual suspected of having CFS/ME is below 500-530 pg/ml (and may be above or below 350-390 pg/ml) and the level of at least one of IL-7, VEGF, CX3CL1, or CXCL9 is below threshold level or level of at least one of CCL24, CCL11, or CCL19 is above threshold levels, the individual may be diagnosed has having CFS/ME.

The analytes (cytokines/chemokines/growth factors) disclosed herein may be used to confirm a clinical diagnosis of CFS/ME. For example, the levels of the analytes may be used to confirm a diagnosis of CFS/ME in a subject. The subject may have been diagnosed as having CFS/ME based on the centre for disease control (CDC) (Fukuda 1994) Definition for CFS/ME, or Canadian Consensus Criteria (CCC) for CFS/ME, or both.

In certain cases, the threshold value represent an approximate level of a biomarker that detects affected subjects at a desired sensitivity (e.g., at least 34%, at least 38%, at least 40%, 45%, 55%, 60%, 70%, or 80% sensitivity or more).

In certain cases, the body fluid sample may be a plasma body fluid sample and the threshold level of IL-16 in plasma may be about 379 pg/ml. This threshold level provides a sensitivity of about 45% and a specificity of about 84%.

In certain cases, the body fluid sample may be a plasma body fluid sample and the threshold level of IL-7 in plasma may be about 9.9 pg/ml. This threshold level provides a sensitivity of about 41% and a specificity of about 80%.

Exemplary embodiments of the present method may include measuring level of VEGF in a body fluid sample of the subject and confirming that the subject has CFS/ME when level of IL-16 is decreased compared to a threshold IL-16 level, level of IL-7 is decreased compared to a threshold IL-7 level, and level of VEGF is decreased compared to a threshold VEGF level.

In certain cases, when more than three biomarkers are measured, the threshold levels for the measured markers used in determining likelihood of CFS/ME may be different than when only two or only one of the markers is measured. For example, when levels IL-16, CXCL9 and CCL19 are measured in a body fluid sample, the threshold level of IL-16 and CXCL9 may be higher than the threshold level when only IL-16 or only CXCL9 is measured.

Biomarkers

As noted in the foregoing sections, measurement of levels of one or more of the biomarkers IL-16, IL-7, VEGF, CX3CL1, CXCL9, CCL24, CCL11, and CCL19 in a body fluid sample of the subject is used in facilitating a diagnosis of CFS/ME in a subject suspected of having CFS/ME.

IL-16

Interleukin 16 (IL-16) is a cytokine released by a variety of cells (including lymphocytes and some epithelial cells) that has been characterized as a chemoattractant for certain immune cells expressing the cell surface molecule CD4. This cytokine is produced as a precursor peptide (pro-IL-16) that requires processing by an enzyme called caspase-3 to become active. Examples of human IL-16 include those comprising an amino acid sequence of Accession No. NP_001165599.1, NP_004504.3, and NP_757366.2 and naturally-occurring variants thereof.

IL-16 detection encompasses detection of full-length IL-16, as well as detection of naturally-occurring fragments or other metabolites of IL-16 found in a biological sample, and detection of fragments or other derivatives generated by manipulation of a biological sample, with the proviso that detection of such fragments, metabolites, or derivatives is specific for detection of IL-16. IL-16 fragments are usually at least 10, 15, 20, 25, 30, 35, 40, 45, 50, 55, or 60 amino acids or more in length. IL-16 may be detected by using an antibody that specifically binds to IL-16 in a body fluid sample of a human subject. Exemplary antibodies include commercially available anti-IL-16 antibody, such as a monoclonal or polyclonal anti-IL-16 antibody available from EMD Millipore, R&D Systems, OriGene, Novus Biologicals, Abcam, Meso Scale Discovery®, and Thermo-Fisher.

IL-7

Interleukin-7 (IL-7) is hematopoietic growth factor capable of stimulating the proliferation of lymphoid progenitors. It is important for proliferation during certain stages of B-cell maturation. Examples of human IL-7 include those comprising an amino acid sequence of Accession No. NP_000871.1 (UniProt Acc. No. P13232-1); NP_001186815.1 (P13232-2), NP_001186816.1 and NP_001186817.1 and naturally-occurring variants thereof.

IL-7 detection encompasses detection of full-length IL-7, as well as detection of naturally-occurring fragments or other metabolites of IL-7 found in a biological sample, and detection of fragments or other derivatives generated by manipulation of a biological sample, with the proviso that detection of such fragments, metabolites, or derivatives is specific for detection of IL-7. IL-7 fragments are usually at least 10, 15, 20, 25, 30, 35, 40, 45, 50, 55, or 60 amino acids or more in length. IL-7 may be detected by using an antibody that specifically binds to IL-7 in a body fluid sample of a human subject. Exemplary antibodies include commercially available anti-IL-7 antibody, such as a monoclonal or polyclonal anti-IL-7 antibody available from R&D Systems, Meso Scale Discovery®, OriGene, and Novus Biologicals.

CXC3CL1

CXC3CL1 is also known as fractalkine and is present in soluble form and membrane bound form. The soluble form is chemotactic for T-cells and monocytes, but not for neutrophils. The membrane-bound form promotes adhesion of those leukocytes to endothelial cells and may play a role in regulating leukocyte adhesion and migration processes at the endothelium. Examples of human CXC3CL1 include those comprising an amino acid sequence of Accession No. NP_002987.1. (UniProt Acc. No. P78423) and naturally-occurring variants thereof.

CXC3CL1 detection encompasses detection of full-length CXC3CL1, as well as detection of naturally-occurring fragments or other metabolites of CXC3CL1 found in a biological sample, and detection of fragments or other derivatives generated by manipulation of a biological sample, with the proviso that detection of such fragments, metabolites, or derivatives is specific for detection of CXC3CL1. CXC3CL1 fragments are usually at least 10, 15, 20, 25, 30, 35, 40, 45, 50, 55, or 60 amino acids or more in length. CXC3CL1 may be detected by using an antibody that specifically binds to CXC3CL1 in a body fluid sample of a human subject. Exemplary antibodies include commercially available anti-CXC3CL1 antibody, such as a monoclonal or polyclonal anti-CXC3CL1 antibody available from R&D Systems, Meso Scale Discovery®, OriGene, and Novus Biologicals.

CCL24

Chemokine (C-C motif) ligand 24 (CCL24) also known as myeloid progenitor inhibitory factor 2 (MPIF-2) or eosinophil chemotactic protein 2 (eotaxin-2). CCL24 is a small cytokine belonging to the CC chemokine family. CCL24 interacts with chemokine receptor CCR3 to induce chemotaxis in eosinophils. CCL24 is also strongly chemotactic for resting T lymphocytes and slightly chemotactic for neutrophils. Examples of human CCL24 include those comprising an amino acid sequence of Accession No. NP_002982.2 (UniProt Acc. Nos. 000175; B2R5K2) and naturally-occurring variants thereof.

CCL24 detection encompasses detection of full-length CCL24, as well as detection of naturally-occurring fragments or other metabolites of CCL24 found in a biological sample, and detection of fragments or other derivatives generated by manipulation of a biological sample, with the proviso that detection of such fragments, metabolites, or derivatives is specific for detection of CCL24. CCL24 fragments are usually at least 10, 15, 20, 25, 30, 35, 40, 45, 50, 55, or 60 amino acids or more in length. CCL24 may be detected by using an antibody that specifically binds to CCL24 in a body fluid sample of a human subject. Exemplary antibodies include commercially available anti-CCL24 antibody, such as a monoclonal or polyclonal anti-CCL24 antibody available from R&D Systems, Meso Scale Discovery®, OriGene, and Novus Biologicals.

CCL19

Chemokine (C-C motif) ligand 19 (CCL19) is a small cytokine belonging to the CC chemokine family that is also known as EBI1 ligand chemokine (ELC) and macrophage inflammatory protein-3-beta (MIP-3-beta). CCL19 is expressed abundantly in thymus and lymph nodes, with moderate levels in trachea and colon and low levels in stomach, small intestine, lung, kidney and spleen. Examples of human CCL19 include those comprising an amino acid sequence of Accession No. NP_006265.1 (UniProt Acc. No. Q99731), and naturally-occurring variants thereof.

CCL19 detection encompasses detection of full-length CCL19, as well as detection of naturally-occurring fragments or other metabolites of CCL19 found in a biological sample, and detection of fragments or other derivatives generated by manipulation of a biological sample, with the proviso that detection of such fragments, metabolites, or derivatives is specific for detection of CCL19. CCL19 fragments are usually at least 10, 15, 20, 25, 30, 35, 40, 45, 50, 55, or 60 amino acids or more in length. CCL19 may be detected by using an antibody that specifically binds to CCL19 in a body fluid sample of a human subject. Exemplary antibodies include commercially available anti-CCL19 antibody, such as a monoclonal or polyclonal anti-CCL19 antibody available from R&D Systems, Meso Scale Discovery®, OriGene, and Novus Biologicals.

VEGF

Vascular endothelial growth factor (VEGF) is a potent angiogenic factor and was first described as an essential growth factor for vascular endothelial cells. VEGF is up-regulated in many tumors and its contribution to tumor angiogenesis is well defined. In addition to endothelial cells, VEGF and VEGF receptors are expressed on numerous non-endothelial cells including tumor cells. Examples of human VEGF include NP_001165094.1 (UniProt. P15692-1); NP_003368.1 (UniProt. P49765-1), NP_001230662.1 (UniProt. P49765-2); NP_005420.1. (UniProt Acc. No. P49767-1); NP_004460.1 (UniProt Acc. No. 043915), and naturally-occurring variants thereof.

VEGF detection encompasses detection of full-length VEGF, as well as detection of naturally-occurring fragments or other metabolites of VEGF found in a biological sample, and detection of fragments or other derivatives generated by manipulation of a biological sample, with the proviso that detection of such fragments, metabolites, or derivatives is specific for detection of VEGF. VEGF fragments are usually at least 10, 15, 20, 25, 30, 35, 40, 45, 50, 55, or 60 amino acids or more in length. VEGF may be detected by using an antibody that specifically binds to VEGF in a body fluid sample of a human subject. The antibody used in the subject methods may specifically bind to VEGF-A, VEGF-B, VEGF-C, or VEGF-D or may specifically bind to an epitope common to VEGF-A, VEGF-B, VEGF-C, and VEGF-D. Exemplary antibodies include commercially available anti-VEGF antibody, such as a monoclonal or polyclonal anti-VEGF antibody available from R&D Systems, Meso Scale Discovery®, OriGene, and Novus Biologicals.

CXCL9

C-X-C motif chemokine 9 (CXCL9) is a cytokine that affects the growth, movement, or activation state of cells that participate in immune and inflammatory response. CXCL9 is chemotactic for activated T-cells and binds to CXCR3. Examples of human CXCL9 include those comprising an amino acid sequence of Accession No. NP_002407.1 (UniProt Acc. No. Q07325-1); and naturally-occurring variants thereof.

CXCL9 detection encompasses detection of full-length CXCL9, as well as detection of naturally-occurring fragments or other metabolites of CXCL9 found in a biological sample, and detection of fragments or other derivatives generated by manipulation of a biological sample, with the proviso that detection of such fragments, metabolites, or derivatives is specific for detection of CXCL9. CXCL9 fragments are usually at least 10, 15, 20, 25, 30, 35, 40, 45, 50, 55, or 60 amino acids or more in length. CXCL9 may be detected by using an antibody that specifically binds to CXCL9 in a body fluid sample of a human subject. Exemplary antibodies include commercially available anti-CXCL9 antibody, such as a monoclonal or polyclonal anti-CXCL9 antibody available from R&D Systems, Meso Scale Discovery®, OriGene, and Novus Biologicals.

CCL11

Chemokine, CC Motif, Ligand 11 (CCL11) is also referred to as "Eotaxin-1" or "E1", Small Inducible Cytokine Subfamily A, Member 11 (SCYA11); and Small Inducible Cytokine A11. CCL11 is produced as prepolypeptide comprising a signal peptide that is cleaved to generate a mature polypeptide. Examples of human CCL11 include those comprising an amino acid sequence of Accession No. P51671; CAG33702.1; NP_002977; and naturally-occurring variants thereof.

E1 detection encompasses detection of full-length E1, as well as detection of naturally-occurring fragments or other metabolites of E1 found in a biological sample, and detection of fragments or other derivatives generated by manipulation of a biological sample, with the proviso that detection of such fragments, metabolites, or derivatives is specific for detection of E1. E1 fragments are usually at least 10, 15, 20, 25, 30, 35, 40, 45, 50, 55, or 60 amino acids or more in length. CCL11 may be detected by using an antibody that specifically binds to CCL11 in a body fluid sample of a human subject. Exemplary antibodies include commercially available anti-CCL11 antibody, such as a monoclonal or polyclonal anti-CCL11 antibody available from R&D Systems, Meso Scale Discovery®, OriGene, and Novus Biologicals.

Detecting and Measuring Biomarkers

Biomarkers, e.g., cytokines/chemokines that may serve as biomarkers according to aspects of the instant disclosure may be detected and/or measured by a variety of different methods that may be chosen and/or tailored to the detection of a particular biomarker or particular biomarkers as desired. Suitable methods of detecting cytokines and chemokines include but are not limited to binding assays, e g, immunoassays, direct detection assays, and proteomic detection assays. Methods of cytokine/chemokine detection may vary and may be either qualitative or quantitative.

Immunoassays useful in detecting analytes (e.g., biomarkers, such as cytokines and chemokines) of the present disclosure may include a binding partner that directly binds to an epitope of the analyte, i.e. an epitope of the particular cytokine or chemokine of interest, and a reporter. In certain embodiments, a body fluid sample of a subject may be contacted with a binding partner that binds to a biomarker present in the body fluid sample. The relationship and interaction between the binding partner and the reporter will vary. Non-exclusive examples of such relationships include instances where the binding partner and the reporter may be covalently bound to one another, may be non-covalently bound to one another, may bind one another at a site that is different from where the analyte binds the binding partner, may bind one another only in the presence of the analyte, may not bind one another, may bind to different epitopes on the same analyte, may bind two different molecules that bind one another, or may be one in the same. Thus, a cytokine/chemokine present in a biological sample can be detected and/or quantified through the binding of epitopes, e.g., novel epitopes and convention epitopes, of the analyte recognized by a binding partner represented by a polyclonal and/or monoclonal antibody, e.g., used in methods such as ELISA, immunoblot assays, flow cytometric assays, immunohistochemical assays, radioimmuno assays, Western blot assays, an immunofluorescent assays, chemiluminescent assays, radioimmunoassays assay and other polypeptide detection strategies.

Typically immunoassays include incubating a biological sample in the presence of an antibody that specifically binds an epitope on the surface of one or more analytes, e.g., polypeptide analytes, e.g., a cytokine polypeptide or a chemokine polypeptide. In some instances a biological sample is brought into contact with an immobilized binding partner, e.g., an antibody, that is immobilized on a solid phase support, carrier, or other solid support or substrate which is capable of immobilizing proteins, immobilizing proteins bound to other proteins, immobilizing proteins bound to other macromolecules, immobilizing proteins bound to cell particles, immobilizing proteins bound to cells, etc.

In other instances, an analyte or a binding partner may be immobilized directly by binding the solid support, e.g., through non-specific adsorption of the analyte to the solid support. In some instances, a binding partner for a particular analyte may be the natural receptor or ligand or portion thereof of the particular analyte. In some instances, a binding partner for a particular analyte may be non-naturally occurring modified versions of the natural receptor of ligand of the analyte, including but not limited to, e.g., a truncated ligand or receptor, a recombinant ligand or receptor, a mutated ligand or receptor, a fusion protein of a ligands, a fusion protein of a receptor, a ligand or receptor or portion thereof modified to comprise a heterologous moiety, or any combination thereof.

Following contacting a biological sample or a portion of a biological sample to a solid support the support may be washed, e.g., with suitable buffers one or more times to remove unbound portions of the biological sample, e.g., unbound protein or unbound analytes. Such solid supports may be of any convenient configuration, including but not limited to, e.g., spherical, as in a bead, or cylindrical, as in the inside surface of a test tube, or the external surface of a rod, Alternatively, the surface may be flat such as a sheet or test strip or the surface of a microscope slide or the bottom surface of a well, e.g., a well of a multi-well plate or a microtiter plate.

In some instances cytokine/chemokine and levels thereof may be detected in a sample by method related to an enzyme linked immunosorbent assay (ELISA), including but not limited to, e.g., an "indirect" ELISA, a "sandwich" ELISA, or a competitive ELISA. Typically in this method, an enzyme is bound to a binding partner, e.g., primary antibody, that binds the analyte, or bound to a secondary binding partner, e.g., a secondary antibody, that binds a primary binding partner that binds the analyte and the enzyme will react with an appropriate substrate. In some instances, the substrate may be a chromogenic substrate, i.e. a substrate that upon interaction with the enzyme, produces a detectable color change.

Any suitable substrate, not limited to e.g., chromogenic substrates, for the enzyme may be used such that the interaction of the enzyme and the substrate produces a chemical moiety which can be detected, e.g., by visual, spectrophotometric, fluorimetric, or other means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Detection and analysis of immunoassays may be performed by any suitable method, including but not limited to, e.g., imaging on a plate-reader, microscopic imaging, photographic imaging, radiographic imaging, exposure to photographic film (e.g., as used in chemiluminescent imaging), and visual inspection.

In some instances, reporters useful in immunoassay include fluorescent labels or fluorescent dyes. Any suitable fluorescent label or dye may be utilized in the detection or measurement of an analyte according to the immunoassay methods described herein. In some instances, fluorescently labels may be attached to a binding partner, e.g., to generate fluorescently labeled binding partners that bind the analyte or fluorescently labeled secondary binding partners that bind a primary analyte binding partner, e.g., primary and secondary antibodies that may be employed in the detection of a cytokine or chemokine analyte. Typically such fluorescent labels are detected by exposing the fluorescent label to light of a particular wavelength allowing for the detection of the label and subsequently the analyte by fluorescence emitted by the fluorescent label exposed to the light of the particular wavelength. Commonly used fluorescent labeling compounds include but are not limited to fluorescein isothiocyanate, rhodamine, phycoerythrin, phycocyanin, allophycocyanin, o-phthaldehyde and fluorescamine, Cy2, Cy3, Cy3B, Cy3.5, Cy5, Cy5.5, and Cy7. Alternatively, chemiluminescent or bioluminescent labels may be employed where suitable.

In some instances, a commercially available immunoassay kits may find use in detection of cytokines and chemokines described herein. Such commercially available kits are well-known in the art and are available from such commercial suppliers as, e.g., EMD Millipore, Qiagen, Life Technologies, Affymetrix, BD Biosciences, Pierce Biotechnology, Enzo Life Sciences, and Abcam. In certain instances, immunoassays, such as those available from commercial suppliers, are multiplexed or arrayed in order to allow the simultaneous analysis of a plurality of cytokines and/or chemokines and, in some instances, may represent a panel of cytokines and/or chemokines for which detection or quantification may be simultaneously performed.

In some instances, cytokine/chemokine and levels thereof may be detected or measured through the use of protein microarray immunoassays. Such protein microarrays are immunoassays that typically utilize small amounts of different purified proteins bound to physically addressable locations on a solid substrate, e.g., a glass or plastic slide, membrane, bead, etc. In some instances, a protein microarray may be an antibody microarray having small amounts of different purified capture antibodies bound to physically addressable locations on a solid substrate, e.g., a glass or plastic slide, membrane, bead, etc. Protein and antibody microarrays may make use of the binding partners, analytes, and reporters and interactions between such binding partners, analytes, and reporters as generally described for immunoassays above. For example, the proteins of a particular biological sample may be labeled with a reporter, e.g., a fluorescent reporter, such that when a particular analyte, e.g., a cytokine/chemokine, binds a particular binding partner of the protein/antibody microarray the analyte may be detected and/or the amount of the analyte may be measured based on the fluorescence detected at the particular physically addressable location of the microarray.

In some instances, commercially available protein or antibody microarrays may find use in methods of detecting and/or measuring cytokine/chemokine levels such as those available from Life Technologies, Cambridge Protein Arrays, Ray Biotech, Promega, Sigma Aldrich, Kerafast, Cell Signaling Technologies, Abcam, and others. In certain cases, such protein microarray detection methods may be combined with other immunoassays or proteomic assays, or direct detection assays as described herein.

In some instances cytokine/chemokine and levels thereof may be directly detected or directly measured in a sample. Methods of direct cytokine/chemokine detection and quantification will vary and in some instances may include mass spectrometry. For example, a sample may be analyzed by generating gas phase ions from the sample, which are then separated according to their mass-to-charge ratio (m/z) and detected. Methods of generating gas phase ions from a sample include electrospray ionization (ESI), matrix-assisted laser desorption-ionization (MALDI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), Fourier-transform ion cyclotron resonance (FT-ICR) analyzers, and combinations thereof (for example, a quadrupole-time-of-flight analyzer, or Q-TOF analyzer). Prior to separation, the sample may be subjected to one or more dimensions of chromatographic separation, for example, one or more dimensions of liquid or size exclusion chromatography or gel-electrophoretic separation. In certain cases, such direct detection methods may be combined with immunoassays or proteomic assays, as described herein.

In some instances cytokine/chemokine and levels thereof may be detected in a sample through the use of proteomic detection assays. Typically proteomic approaches to analyte detection include analysis of all or a majority of all or at least a plurality of the proteins present in a particular organism or a particular sample from a particular organism. Such analyses may vary and may include but are not limited to analyses of the presence or absence of one or more proteins, changes in one or more proteins, e.g., post-translation modifications, or the interaction of particular proteins as determined by evaluating the proteome of an organism or a sample as a whole. In some instances, the proteome of an organism or the proteome of a particular sample, e.g., a plasma proteome, may be evaluated by a proteomic method including two-dimensional differential gel electrophoresis, e.g., fluorescent two-dimensional differential gel electrophoresis, or a proteome protein microarray (i.e. protein chips). In some instances, a commercially available proteome cytokine and chemokine array kit may be used as such kits are available from such suppliers as, e.g., R&D systems. In certain cases, immunoassays or direct detection methods, as described herein, may be combined with proteomic methods, e.g., in order to facilitate cytokine/chemokine identification or quantification.

Detection, analysis, and/or quantification of cytokines/chemokines as performed by the cytokine/chemokine detection methods, as described herein, may further include an evaluation of the results of the assay by comparison to a control or reference standard. For example, in some instances, the results of a particular immunoassay, direct detection assay, or proteomic assay are compared to a reference standard, e.g., a control or a standard. Any suitable control or standard for a particular immunoassay, direct detection assay, or proteomic assay may be employed including control assays performed concurrently with or immediately before or after the detection assay (e.g., internal or external control assays or reactions). Such control assays will vary but may include providing with the assay a known concentration or known amount of one or more of the analytes to be detected or measured, e.g., a positive control. In some instances, a control assay may include a number of different known concentrations of a particular analyte such that qualitative assessments of the amount of the analyte present in the sample may be made by comparison to the control assay results with the various known concentrations. In some instances, control assays for a particular immunoassay, direct detection assay, or proteomic assay need not necessarily require performing a control assay or control reaction and may instead make use of the results of previously performed control reactions. In some instances, such results may be provided as reference results or reference standards, e.g., as a single values (i.e. a threshold), as a range of values, as multiple values provided in a table, in a chart, in a graph, as an image or illustration or diagram of an assay result, e.g., a picture of a positive result or negative result or pictures of particular quantitative or qualitative results.

In certain cases, a normalizing protein, for example, a housekeeping protein such as β-actin may also be detected simultaneously or in parallel and used to normalize the biomarker protein levels.

"Normalized level" refers to level of a biomarker of CFS/ME disclosed herein relative to level of a normalizing protein(s), such as a housekeeping protein. In certain cases, the measuring of a biomarker in a body fluid sample of a subject suspected of having CFS/ME may include determining a normalized level of the biomarker. In other embodiments, the level may not be normalized.

As used herein, the term "level" in the context of a biomarker disclosed herein refers to the amount of a protein in a body fluid sample of a subject. The level may be an actual level (e.g., concentration) or a relative level or a semi-quantitative level. In other embodiments, the level may the actual concentration of the biomarker.

Subjects

The methods of the present disclosure can be used to facilitate a diagnosis of CFS/ME in a subject suspected of having CFS/ME. A subject may be suspected of having CFS/ME based on a clinical diagnosis guided by physical symptoms exhibited by the subject and/or physical symptoms reported by the subject. For example, a subject may be suspected of having CFS/ME if the subject has been clinically diagnosed based on the Center for Disease Control (CDC) Fukuda 1994 Criteria for CFS/ME, or Canadian Consensus Criteria (CCC) for CFS/ME, or both.

In certain cases, a subject suspected of having CFS/ME may be a subject who has physicals symptoms related to CFS/ME, such as, fatigue that is not improved by rest, and/or may be worsened by physical activity. For example, a subject suspected of having CFS/ME may suffer from unexplained persistent or relapsing chronic fatigue that is of new or definite onset (i.e., not lifelong), is not the result of ongoing exertion, is not substantially alleviated by rest. In addition, the subject may exhibit four or more of the following symptoms: impairment in short-term memory or concentration; sore throat; tender lymph nodes; muscle pain; multi-joint pain without swelling or redness; headaches of a new type, pattern, or severity; unrefreshing sleep; and post-exertional malaise lasting more than 24 hours.

In certain cases, a subject suspected of having CFS/ME may be a subject who has new onset, unexplained, persistent, or recurrent physical and mental fatigue that substantially reduces activity level; inappropriate loss of physical and mental stamina, rapid muscular and cognitive fatigability, post exertional malaise and/or fatigue and/or pain; unrefreshed sleep or sleep quantity or rhythm disturbances such as reversed or chaotic diurnal sleep rhythm; significant degree of myalgia (in the muscles and/or joints/significant headaches of new type, pattern or severity); two or more neurological/cognitive manifestations: confusion, impairment of concentration and short term memory consolidation, disorientation, difficulty with information processing, categorizing and word retrieval, and perceptual and sensory disturbances—e.g., spatial instability and disorientation and inability to focus vision.

In certain cases, a subject suspected of having CFS may not be a subject who has a chronic disease that is accompanied with fatigue such as cancer, muscular dystrophy, cachexia, sarcopenia, neurodegenerative disease, and the like, or a subject diagnosed with Gulf War Illness (GWI).

Compositions

The present disclosure provides compositions that find use, e.g., in practicing the methods of the present disclosure. In certain aspects, the compositions include an agent for detecting a biomarker of interest. For example, the detection agent may be a reagent that specifically detects a biomarker of interest.

Exemplary compositions include an antibody that specifically binds to IL-16 in a body fluid sample of a human subject. In certain embodiments, the composition may include an anti-IL-16 antibody and an anti-IL-7 antibody. In other embodiments, the composition may include an anti-IL-16 antibody, an anti-IL-7 antibody, and an anti-VEGF antibody. In other embodiments, the composition may include different antibodies each of which specifically binds to a biomarker disclosed herein.

The detection agent may be present in a liquid form or a lyophilized form. In certain cases, the compositions of the present disclosure may include one or more antibodies that specifically bind to the biomarkers disclosed herein and a buffer.

According to certain embodiments, the composition may include a detection agent for detecting a control (e.g., "housekeeping") protein.

In certain aspects, the compositions of the present disclosure are present in a container, such as a storage container and/or assay container. The container may be any convenient container convenient, e.g., for storing an IL-16 detection agent (e.g., in combination with one or more detection agents for detecting IL-7, VEGF, CXCL9, CX3CL1, CCL11, CCL19 or CCL24, or any combination thereof), or for carrying out a detection assay (e.g., a solution- or solid phase-based assay) for detecting IL-16 and any additional biomarker(s) of interest, such as IL-7, VEGF, CX3CL1, CXCL9, CCL11, CCL19 or CCL24, or any combination thereof. Containers of interest include a tube, e.g., a tube of any convenient size (e.g., ranging from 0.2 ml to 15 ml, such as 0.2 ml, 0.5 ml, 1.0 ml, 1.5 ml, 2.0 ml, 5 ml, 10 ml, 15 ml or the like) and material (e.g., polypropylene, or any other material suitable for storing or using the composition). In certain aspects, the composition is present in a container that is a series of chambers, such as a one- or two-dimensional array of tubes (e.g., a strip of tubes, or tubes in a "plate" format, such as a 24-well, 48-well, 96-well, 384-well, or other convenient plate format).

According to certain embodiments, the composition is disposed on a planar substrate (e.g., the bottom of a well, array, chip (e.g., microfluidic chip), and/or the like). When the composition is disposed on a substrate, any detection agents present in the composition (e.g., an IL-16 detection agent, optionally in combination with any one or more of an IL-7, VEGF, CX3CL1, CXCL19, CCL11, CCL19 or CCL24 detection agent) may be present in a solution or suspension disposed on the substrate, or alternatively, may be attached to the substrate, e.g., directly attached to the surface of the substrate, or attached via a linker moiety (e.g., an antibody (such as an anti-species antibody) or other suitable linker moiety). Such compositions find use, for example, in performing solid phase assays (e.g., ELISA-based or non-enzyme-based solid phase protein detection assays, solid-phase nucleic acid amplification, or the like) for detecting one or more biomarkers of interest.

Biological Samples

Suitable biological samples useful in the methods of the present disclosure include biological fluids (e.g., a blood sample, e.g., whole blood, blood fraction (e.g., serum, plasma)), and other liquid samples of biological origin.

Where the biological sample is a blood sample, the blood sample can be obtained from fresh blood or stored blood (e.g. in a blood bank). The biological sample can be a blood sample expressly obtained for an assay of the present disclosure or a blood sample obtained for another purpose which can be subsampled for an assay of the present disclosure.

Samples can be manipulated after procurement, such as by treatment with reagents, solubilization, and/or enrichment for certain components for an analyte (s) to be assayed. Samples can be pretreated as necessary by dilution in an appropriate buffer solution, concentrated if desired, or fractionated by any number of methods including but not limited to ultracentrifugation, fractionation by fast performance liquid chromatography (FPLC), or precipitation. Any of a number of standard aqueous buffer solutions, employing one of a variety of buffers, such as phosphate, Tris, or the like, at physiological pH can be used. In certain embodiments, after isolation, samples (such as blood samples) are stored at 4° C., −20° C. or at −80° C. until assaying.

In certain embodiments, the circulating levels of the analytes disclosed herein for diagnosis of CFS/ME are measured. In certain cases, the analytes are detected in the liquid fraction of the body fluid sample, such as, in the liquid fraction of whole blood and not in cells, such as blood cells.

Examples of Applications of Method Results

The methods of the present disclosure can provide results which can then be applied to facilitate decisions as to the care of the subject. Examples are provided below.

Assay-Guided Therapy and Monitoring of Therapy

The methods of the present disclosure can facilitate a clinician in making a treatment decision for the subject, e.g., whether the results of the method suggest the subject may or may not benefit from therapeutic intervention for treatment of CFS/ME. For example, if a patient has elevated levels of CCL11, CCL19 or CCL24, an antibody therapy to these proteins alone or in combination may be a used for treatment of CFS/ME. In certain embodiments, a patient may be diagnosed as having CFS/ME using the methods described herein. Following diagnosis, the patient may be administered an anti-CCL11 antibody, an anti-CCL19 antibody, an anti-CCL24 or a combination thereof in order to mitigate the effect of elevated levels of these proteins.

In certain cases, a CFS/ME patient may have elevated level of CCL11. The CFS/ME patient may be treated by administering an anti-CCL11 antibody. In certain cases, a CFS/ME patient may have elevated level of CCL19. The CFS/ME patient may be treated by administering an anti-CCL19 antibody. In certain cases, a CFS/ME patient may have elevated level of CCL24. The CFS/ME patient may be treated by administering an anti-CCL24 antibody.

Administering of the antibody may be via any appropriate route. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation.

The methods of the present disclosure can facilitate monitoring therapy of a subject undergoing treatment. For example, where the subject is receiving a therapy, the method can provide a method of monitoring therapy. In this case, the method results can guide a clinician in adjusting therapy (e.g., whether or not to continue therapy (e.g., so as to avoid relapse), increase or decrease dose, change therapy regimen (e.g., from monotherapy to combination therapy, or from non-surgical therapy to surgical therapy) where the patient is not receiving adequate therapeutic benefit (e.g., the patient is not responding to therapy), and the like). Such methods of monitoring therapy are useful in guiding further treatment decisions, such as whether continued administration of a drug regimen indicated, or whether the patient should receive a different therapy. The methods of monitoring therapy using the algorithms of the present disclosure may be used in combination with other methods for assessing whether a subject responds to therapy (is a "responder") or is not exhibiting a sufficient therapeutically beneficial response (is a "nonresponder").

Identifying Subjects for Clinical Trial Populations

The methods of the present disclosure find use in identifying subjects suitable for inclusion or exclusion in a clinical trial based on upon the likelihood the subject has CFS/ME. For example, the methods of the present disclosure can be used to identify subjects suitable for inclusion in a clinical trial to assess efficacy of a drug on treatment of CFS/ME, so that subjects that do not have CFS/ME are excluded. In another example, the methods of the present disclosure can be used to identify subjects having one or more of CFS/ME so as to excluded such subjects from a clinical trial (e.g., where the clinical trial is to assess efficacy of a drug for a disease other than CFS/ME). Such methods can facilitate identification of drugs or other therapies for treatment of CFS/ME.

Kits

Kits of the present disclosure can include a binding reagent(s) for one or more, two or more, three or more or for each of IL-16, IL-7, VEGF, CX3CL1, CXCL9, CCL24, CCL11, and CCL19. The binding reagent can be, for example, and antibody that specifically binds a biomarker (e.g., an anti-IL-16 antibody, anti-IL-7 antibody, and anti-VEGF antibody, an anti-CCL19 antibody). In some embodiments, the kit includes a binding reagent for IL-16 analyte and a reagent(s) for detection of the analyte-binding reagent complex. The reagent(s) for detection of the analyte-binding reagent complex can be a second binding reagent, e.g., an anti-analyte antibody or an anti-binding reagent antibody. "Binding reagent" as used here encompasses both capture reagents and detection reagents. A "capture reagent" refers to a binding partner for a biomarker that is suitable for use in, for example, enriching a sample for its respective biomarker, e.g., an anti-biomarker antibody. Where the capture reagent comprises an antibody, the antibody may be a polyclonal or monoclonal antibody. "Detection reagent" refers to a binding partner for a biomarker that is suitable for use in detection of an immobilized biomarker, e.g., an anti-biomarker antibody, and is optionally detectably labeled. Where the detection reagent comprises an antibody, the antibody may be a polyclonal or monoclonal antibody. Kits may further include one or more reagents for detection of binding of a detection reagent, e.g., detection of an anti-biomarker antibody, e.g., as when bound to an anti-biomarker binding reagent/biomarker complex.

Capture reagents provided in a kit of the present disclosure can be immobilized on an insoluble support, e.g., an assay substrate, such as an array, bead, and the like as described herein. Detection reagents can include a detectable label. Where the detection reagents are not detectably labeled, the kit can include reagents for detecting the detection reagents, such as an antibody.

Kits can include instructions for using the components of the kit to practice a method of the present disclosure. The instructions are generally recorded on a suitable recording medium, such as paper, plastic, electronic storage medium, and the like. For example, the instructions may be present in the kits as a package insert, in the labeling of the container of the kit or components thereof (e.g., associated with the packaging or subpackaging) etc. In other embodiments, the instructions are present as an electronic storage data file present on a suitable computer readable storage medium, e.g. compact disc-read only memory (CD-ROM), digital versatile disk (DVD), diskette, etc. In other examples, the instructions provided do not contain many or all assay details, but rather provide direction as to a remote source for obtaining detailed instructions, e.g. via the internet.

Reports

The methods of the present disclosure can include generating a report indicating the results of the method and providing guidance as to how the results might be applied to the care of the subject. A "report," as described herein, refers generally to an electronic document or file (e.g., pdf file, monitor display), as well as a tangible document (e.g., paper report). A subject report can be completely or partially electronically generated, e.g., presented on an electronic display (e.g., computer monitor).

The method results in the report can include, for example, one or more of the level of the biomarker(s) assayed. The level can be reported as a quantitative score (e.g., a concentration, e.g., pg/ml serum or plasma) and/or a semi-quantitative score (e.g., a score reflecting an amount of a biomarker relative to a control level or a selected threshold level). The method results can optionally include assay results for a control biomarker.

Reports can include information such as a predicted risk that the patient has CFS/ME or does not have CFS/ME. In certain cases, the report includes an assessment that the subject has or does not have CFS/ME.

In certain cases, the report may include results of the measured level(s) of biomarker(s); a threshold level or a normal level for the biomarker(s) and an assessment of likelihood of CFS/ME. A reader of the report, e.g., a clinician may analyze the results and provide a written and/or verbal diagnosis of presence or absence of CFS/ME.

Reports can include guidance to a clinician as to a treatment recommendation for the subject based on the likelihood of the presence or absence of CFS/ME. For example, reports can include a recommendation regarding further evaluation and/or avoiding expensive and invasive evaluations and/or a recommendations regarding therapeutic intervention (e.g., administering a drug, recommending surgical intervention, etc.), modifying a treatment regimen (e.g., adjusting a drug dose (e.g., increasing or decreasing a dose), adjusting a dosage regimen (e.g., increasing or decreasing dose frequency and/or amount), and the like.

A report can further include one or more of: 1) patient information (e.g., name, medical information (e.g., age, gender, symptoms (e.g., symptoms that may be relevant to diagnosis of CFS/ME), etc.), 2) information about the biological sample (e.g., type, when obtained); 3) information regarding where and how the assay was performed (e.g., testing facility, assay format); 4) service provider information; and/or 5) an interpretive report, which can provide a narrative providing an at least partial interpretation of the results so as to facilitate a diagnosis by a clinician.

Accordingly, the methods disclosed herein can further include a step of generating or outputting a report providing the method results and, optionally, other information such as treatment guidance as described herein. The report can be provided in the form of an electronic medium (e.g., an electronic display on a computer monitor), or in the form of a tangible medium (e.g., a report printed on paper or other tangible medium). An assessment as to the likelihood can be referred to as "risk report" or, simply, a "diagnostic result". The person or entity that prepares a report ("report generator") may also perform steps such as sample gathering, sample processing, and the like. Alternatively, an entity other than the report generator can perform steps such as sample gathering, sample processing, and the like. A report can be provided to a user. A "user" can be, for example, a health professional (e.g., a clinician, a laboratory technician, a physician, etc.).

Computer-Implemented Methods, Systems and Devices

The methods of the present disclosure can be computer-implemented, such that method steps (e.g., assaying, comparing, calculating, and/or the like) are automated in whole or in part. Accordingly, the present disclosure provides methods, computer systems, devices and the like in connection with computer-implemented methods of facilitating a diagnosis of CFS/ME.

For example, the method steps, including obtaining values for biomarker levels, comparing biomarker levels to a control level, generating a report, and the like, can be completely or partially performed by a computer program product. Values obtained can be stored electronically, e.g., in a database, and can be subjected to an algorithm executed by a programmed computer.

For example, the methods of the present disclosure can involve inputting a biomarker level into a computer programmed to execute an algorithm to perform the comparing and calculating step(s) described herein, and generate a report as described herein, e.g., by displaying or printing a report to an output device at a location local or remote to the computer.

The present invention thus provides a computer program product including a computer readable storage medium having a computer program stored on it. In certain aspects, the storage medium is non-transitory (e.g., a storage medium that is not a transitory wave or signal). The program can, when read by a computer, execute relevant calculations based on values obtained from analysis of one or more biological sample from an individual. The computer program product has stored therein a computer program for performing the calculation(s).

The present disclosure provides systems for executing the program described above, which system generally includes: a) a central computing environment; b) an input device, operatively connected to the computing environment, to receive patient data, wherein the patient data can include, for example, biomarker level or other value obtained from an assay using a biological sample from the patient, as described above; c) an output device, connected to the computing environment, to provide information to a user (e.g., medical personnel); and d) an algorithm executed by the central computing environment (e.g., a processor), where the algorithm is executed based on the data received by the input device, and wherein the algorithm calculates a value, which value is indicative of the likelihood the subject has CFS/ME as described herein.

The present disclosure provides methods for treating CFS/ME in a subject. In certain cases, a CFS/ME patient having an elevated level of at least one of the analytes: CCL24, CCL11, and CCL19 may be treated by administering an effective amount of an antagonist(s) of the analyte(s) that is (are) elevated. In certain embodiments, the subject may have been diagnosed as having CFS/ME using the methods disclosed herein. In other cases, the subject may be suspected of having CFS/ME due to presence of symptoms associated with CFS/ME. The level of CCL24, CCL11, and/or CCL19 may be determined in a body fluid sample of a patient having or suspected of having CFS/ME by the methods disclosed herein or an art accepted method. In certain cases, a CFS/ME patient may have been determined to have elevated level of CCL24 by assaying a body fluid sample of the patient. The CFS/ME patient with elevated level of CCL24 may be treated for CFS/ME by administering an effective amount of an antagonist of CCL24 or a receptor of CCL24. In another case, the subject may have been determined to have elevated level of CCL11 by assaying a body fluid sample of the patient. The CFS/ME patient with elevated level of CCL11 may be treated for CFS/ME by administering an effective amount of an antagonist of CCL11 or a receptor of CCL11. In another case, the subject may have been determined to have elevated level of CCL19 by assaying a body fluid sample of the patient. The CFS/ME patient with elevated level of CCL19 may be treated for CFS/ME by administering an effective amount of an antagonist of CCL19 or a receptor of CCL19. As noted previously, when two or all three of the analytes are elevated, antagonists of the two or all three of the analyte may be administered to treat CFS/ME. The antagonists may be administered simultaneously or sequentially.

"Antagonist" as used herein refers to a drug (e.g., antibody) that reduces or blocks activity of its target. Representative antagonists, include, but are not limited to, antibodies (including antigen-binding antibodies), nucleic acids (e.g., antisense molecules, such as ribozymes and RNA interfering agents), immunoconjugates (e.g., an antibody conjugated to a therapeutic agent), small molecule drug inhibitors, fusion proteins, aptamers, and the like. Reduction of activity of a target (e.g., CCL24, CCL11, or CCL19) can be accomplished by, for example, reducing an amount of active target present in the bloodstream of a subject or reducing the amount of CCL24, CCL11, or CCL19 expressed in cells of the subject, and/or reducing activity of the target.

In one embodiment, the antagonist is an antibody or an antigen-binding fragment of an antibody that specifically binds and blocks the activity of the elevated analyte or its receptor. In certain embodiments, the antibody or an antigen binding fragment thereof may be a chimeric antibody or a humanized antibody. In one embodiment, the antagonist is an antibody or an antigen-binding fragment of an antibody that specifically binds a receptor for the elevated analyte and blocks the analyte from binding the receptor.

In another embodiment, the CCL24, CCL11, or CCL19 antagonist is a small molecule. As used herein, "small molecule" refers to synthetic chemical molecules that are less than about 1000 daltons in molecular weight, such as less than 750 daltons, including molecules less than 700 daltons, and inhibit activity of the target. In certain cases, the antagonist may be a protein that competes with the elevated analyte for binding to its receptor.

In certain cases, the methods of treatment involve identifying a subject as having CFS/ME, and administering an amount of a CCL24 antagonist and/or a CCL19 antagonist and/or a CCL11 antagonist, effective to provide a therapeutic benefit in the patient. "Therapeutic benefit", "treat", "treatment" includes at least reduction the severity of, or amelioration of one or more symptoms of a disease.

Also disclosed herein are methods for treating CFS/ME patients that have reduced level of one or more of analytes: IL-16, IL-7, VEGF, CX3CL1, and CXCL9 by administering the analyte that is reduced in the patient in an amount effective to provide a therapeutic benefit to the patient. For example, a CFS/ME patient with decreased level of IL-16 may be treated by administering an effective amount of IL-16 or an active fragment thereof. A CFS/ME patient having reduced levels of two or more of the analytes: IL-16, IL-7, VEGF, CX3CL1, and CXCL9, in a body fluid, such as, blood, may be administered the analytes sequentially or simultaneously. The administered analyte may have modifications to increase its half-life.

The phrase "effective amount" or "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological/physical effects. An effective dose (ED) is the dose or amount of an agent that produces a therapeutic response or desired effect in some fraction of the subjects taking it. The effective dose of the antagonists or the analytes disclosed herein may be determined by a clinician.

Administering of the aforementioned therapy for treatment of CFS/ME may be via any appropriate route. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation.

In certain cases, the level of an analyte may be determined to be elevated when it is higher than a normal level or normal range of level of the analyte. The level of an analyte may be determined to be reduced when it is below than a normal level or normal range of level of the analyte. In certain cases, the level of an analyte may be determined to be elevated when it is higher than a threshold level for the analyte. In certain cases, the level of an analyte may be determined to be reduced when it is lower than a threshold level for the analyte.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Patients:

The plasma samples of one hundred CFS/ME patients and seventy-nine healthy individuals are kindly provided by Solve Myalgic Encephalomyelitis/Chronic Fatigue Syndrome (ME/CFS) Initiative (formerly known as Chronic Fatigue and Immune Dysfunction Syndrome [CFIDS] Association of America) which were clinically diagnosed based on case definition criteria of 1994 centre for disease control (CDC) Fukuda Criteria for CFS/ME (Annals of internal medicine 121, 953-959) as well as the Canadian Consensus Criteria (CCC). Gender and age matched controls were included along with the cases (Table 1):

TABLE 1

Number, sex, and age of subjects in the study

|  | Controls | CFS |
| --- | --- | --- |
| Number of subjects | 79 | 100 |
| Sex (F/M) | 62/17 | 72/28 |
| Age (mean +/− SD) | 50.4 +/− 12.6 | 50.5 +/− 12.6 |

Controls = Healthy controls,
CFS = Chronic Fatigue Syndrome patients,
SD = Standard deviation,
M = Male, and
F = Female.

Technology and Detection System:

Pre-coated multiplex ELISA plates from Meso Scale Discovery (MSD, Gaithersburg, Mass., USA) were selected for assays after a rigorous comparison with other technologies for their sensitivity at low concentrations, linearity and high dynamic range of the standard curves, as well as inter-plate low variability. MSD Kits employed were Human V-PLEX Plus Kits including Chemokine Panel 1 (Catalog No. K15047D), Cytokine Panel 1 (Catalog No. K15054G), Pro-inflammatory Panel 1 (Catalog No. K15049G), Human Eotaxin-2 Kit (Catalog No. K151RKD), a custom-designed 3-Plex kit (Catalog No. N451A), and a β2M custom-designed 1-Plex kit (Catalog No. N45CA). The list included CCL11, CCL24, eoatxin-3 (CCL26), IL-8, interferon gamma-induced protein 10 (IP-10; CXCL10), monocyte chemotactic protein-1 (MCP-1; CCL2), monocyte chemotactic protein-4 (MCP-4; CCL13), macrophage-derived chemokine (MDC; CCL22), macrophage inflammatory protein-1-alpha (MIP-la; CCL3), macrophage inflammatory protein-1-beta (MIP-1β; CCL4), thymus and activation regulated chemokine (TARC; CCL17), granulocyte-macrophage colony-stimulating factor (GM-CSF), IL12/23p40, IL-15, IL-16, IL-17, IL-la, IL-5, IL-7, tumor necrosis factor beta (TNF-β), VEGF, interferon (IFN)-γ, IL-10, IL-12p70, IL-13, IL-1β, IL-2, IL-4, IL-6, TNF-α, CX3CL1, CXCL9, CCL19, and $β_2$ microglobulin. Frozen plasma samples (stored at −80° C.) from healthy controls and CFS/ME patients were assayed in duplicate immediately after the first thaw. All experiments were performed according to the manufacturer's instructions with minimal modifications and optimization as described before (Landi et al., 2014). Briefly, 50 μl of each 1:2 diluted sample was added to each well of the pre-coated 96-well plate and incubated at room temperature (RT) for 2.5 hours with continuous counter-clock-wise shaking. The plates were then washed three times with 1× Wash Buffer (MSD) and Sulfotag Detection Antibody Cocktail (MSD) was then added to each well and the plates then incubated for an additional 2 hours with shaking at RT. Finally, the plates were washed again, and were scanned by a SECTOR® Imager 6000 Reader (MSD) after adding 150 μl of 2× Read Buffer (MSD).

Data Pre-Processing:

To accurately quantify the concentrations of each analyte in the test samples, a four-point logarithmic standard curve was used based on a commonly accepted method of "Fit-for-Purpose Method Development and Validation for Successful Biomarker Measurement" (Lee et al., 2006, Pharm Res 23, 312-328). To measure the Intra-plate coefficient variance (Intra-CV), we added four standard samples at different concentrations to each plate. Intra-CVs were calculated for each plate and the average of all the plates are reported for each analyte. The lower level of detection (LLOD) was calculated based on the mean of negative control samples +2.5 standard deviations (SD). The lower level of quantification (LLOQ) was set to the lowest standard sample value on the linear part of the standard curve, where it's "Mean Recovery Value" was within 20% of the actual value (accuracy of 20%) with a CV of 20% (precision of 20%) for the given standard curve point. When the signals obtained by the scanner were plotted against the calculated concentrations for each standard and control sample (data not shown), any adverse matrix effect was ruled out as the concentration curves for both standard and control samples were highly correlated, and comparable with the signal reported by the scanner. The determined concentrations were also corrected for dilution prior to statistical analysis.

Statistical Analyses:

A. Hypothesis Testing:

The data in each group (CFS/ME & Controls) for individual analytes were not normally distributed, thus for each analyte in turn, the null hypothesis that there was no difference in population median values between CFS/ME groups was tested using the Mann-Whitney U test. Correction for multiple comparisons was performed using Storey's FDR methodology (Storey, 2002, Journal of the Royal Statistical Society Series B 64, 479-498). Both p-values and corrected q-values are reported. The linear correlation between all reproducibly measured analytes was calculated using the non-parametric pairwise Pearson's correlation coefficient. The resulting correlation matrix is presented in the form of a spring-embedded correlation plot (Broadhurst, 2006, Official journal of the Metabolomic Society 2, 171-196). Here a network of "nodes" and "spring-edges" are constructed such that each node represents each of the tested analytes and the spring constant of each edge is proportional to the correlation coefficient between two connected nodes. The size of each node is proportional to significance of that variable; the larger the node the lower the p-value. Edges were only included in the network if the correlation coefficient was positive, and significant at a critical p-value of 0.05. Once the network is constructed it is allowed to "relax". That is, the connected spring-edges compete against each other to pull the nodes in a given direction based on the spring constant (the higher the correlation, the stiffer the spring, and hence the more power organizing the clustering of the node). Once relaxed (i.e. the model is in a low energy configuration) the spring embedded plot can be viewed as a simple multivariate cluster analysis, where nodes that cluster close to each other can be considered to be highly correlated in a multivariate sense. Node color directly maps both the level of significance and whether the median CFS/ME concentration was higher or lower than median control (Red=p<0.05 and CFS/ME>Control; Orange=p<0.1 and CFS/ME>Control; Blue=p<0.05 and Control>CFS/ME; Light Blue=p<0.1 and Control>CFS/ME; nodes were colored grey when their corresponding p-value was >0.1). Networks were constructed using the graph visualization software—Graphviz using the 'neato' virtual physics model (Ellson J., 2004, Graphviz and Dynagraph—static and Dynamic Graph Drawing Tools. Springer-Verlag, Berlin/Heidelberg).

B. Multivariate Data Analysis:

To investigate the potential utility of combining multiple analytes into a single model predictive of CFS/ME, two techniques were compared: Logistic Regression optimized by LASSO regularization (LASSO-LR), and Classification And Regression Trees (CART). Logistic Regression is a type of probabilistic statistical classification model commonly used for predicting the outcome of a categorical dependent variable (in this case CFS/ME vs. Control), and can be considered as a as a special case of a generalized linear model of the form: $\log it(p_i)=\beta_0+\beta_1 x_{1,i}+\beta_2 x_{2,i} \ldots +\beta_m x_{m,i}$ (where, $p_i$ is the predicted probability of positive classification for the $i^{th}$ patient, $x_{1,i} \ldots x_{m,i}$ are the m analyte measurements for the $i^{th}$ patient, $\beta_0$ is the regression constant, and $\beta_1 \ldots \beta_m$ are regression coefficients indicating the relative influence of a particular analyte on the outcome). In complete contrast, CART is a non-parametric decision tree model that produces (in this case) a classification tree as a predictive model. A decision tree can be translated in to a simple set of logical rules for classification such as: if $(x_{1,i}>a)$ AND $(x_{2,i}<b)$ then $y_i=1$, else $y_i=0$.

Both methodologies were optimized in order to produce a robust and parsimonious model. The LR model was optimized using LASSO regularization (Hastie, 2008, Springer, New York), and the CART model was optimized using tree "pruning" (Breiman, 1984, Classification and Regression Trees. CRC Press, Boca Raton, Fla.). For each method, 5-fold cross-validation with 100 Monte Carlo repetitions was performed during the optimization to ensure the avoidance of "over fitting" (i.e. ensuring the model is generalizable for future testing with new independent samples). The resulting optimal classifier models were assessed using Receiver Operator Characteristic (ROC) curve analyses. This allows determination a posteriori of the optimal "decision boundary" (the predictive score determining whether a sample is classified as CFS/ME rather than control) and the associated optimal classification sensitivity and specificity. The area under the ROC curve (AUC) is used as a generalized non-parametric estimate of biomarker utility (AUC=1 implies a perfect classifier; AUC=0.5 implies a model which is no better than flipping a coin to determine outcome). Bootstrap resampling was performed (n=500) to estimate the 95% confidence interval (CI) for both the AUC, and a given model's optimal sensitivity given a fixed specificity.

All statistical analysis was performed using Matlab® scientific scripting language, version R2014b. The Logistic Regression model was verified using STATA® statistical software, version 13.

Results

Study Population:

One hundred patients diagnosed with CFS/MS were recruited for this study; subsequently 79 gender and age matched healthy controls were recruited. The details of patient demographics are summarized in Table 1 (above). There was no significant difference in gender proportions, or age, between these two groups.

Univariate Analysis:

The concentration of 34 plasma cytokines, chemokines and growth factors were measured in each test subject using Multiplex Elisa Assays. FIG. 1 describes for each measured analyte, the median measured concentrations for each group, the significance of the difference between CFS/ME and Control populations, the Intra-/Inter-CVs, the LLOD, the LLOQ and the percentage of measured concentrations below the LLOD and LLOQ.

Analytes with any measured concentrations below the LLOQ were removed from subsequent data analysis, leaving 18 reliably quantified analytes. As shown in FIG. 1, eight analytes were correlated to presence of CFS/ME. Five analytes had significantly decreased levels in CFS/ME patients (IL-16, IL-7, VEGF, CXCL9, CX3CL1) and three analyte were significantly increased (CCL24, CCL19, and CCL11). Percent sensitivity and specificity of IL-16, IL-7, VEGF, CCL24, CCL19, CXCL9, and CX3CL1 in detecting presence of CFS/ME are provided in FIG. 2. FIG. 2A shows that an IL-16 plasma level of less than 379 pg/ml is correlated to presence of CFS/ME with 45% sensitivity and 84% specificity; an IL-7 plasma level of less than 9.9 pg/ml is correlated to presence of CFS/ME with 41% sensitivity and 80% specificity; a VEGF plasma level of less than 74 pg/ml is correlated to presence of CFS/ME with 40% sensitivity and 78% specificity; a CCL24 plasma level of more than 1836 pg/ml is correlated to presence of CFS/ME with 41% sensitivity and 77% specificity; a CCL19 plasma level of more than 117 pg/ml is correlated to presence of CFS/ME with 34% sensitivity and 77% specificity; a CXCL9 plasma level of less than 320 pg/ml is correlated to presence of CFS/ME with 44% sensitivity and 77% specificity; and a CX3C1 plasma level of less than 2800 pg/ml is correlated to presence of CFS/ME with 38% sensitivity and 77% specificity. FIG. 2B shows that an IL-16 plasma level of less than 379 pg/ml and an IL-7 plasma level of less than 9.9 pg/ml is correlated to presence of CFS/ME with 25% sensitivity and 98% specificity. Thus, when both IL-16 and IL-7 levels in plasma samples are assayed, 25 out of 100 CFS/ME patients are correctly diagnosed with CFS/ME and only 2 out of 100 control subjects are misdiagnosed as having CFS/ME.

Figure 3B:
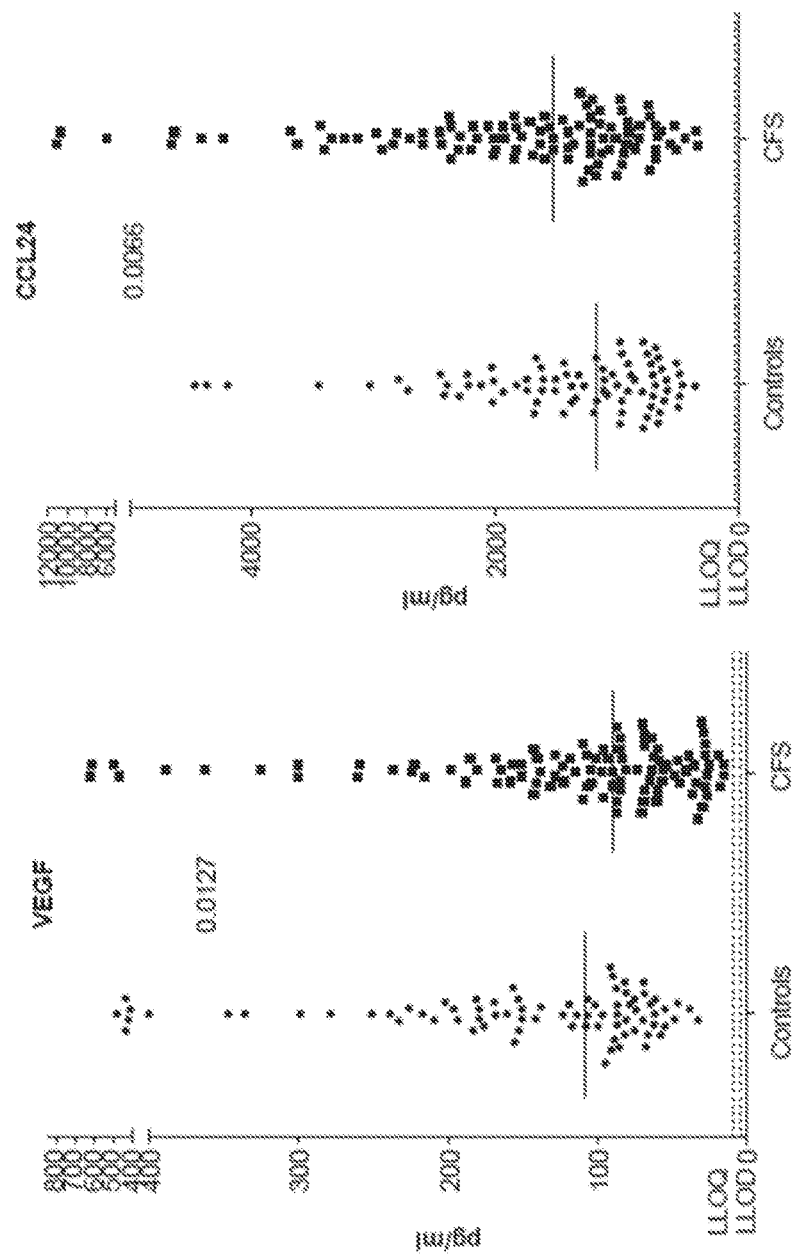
Figure 3C:
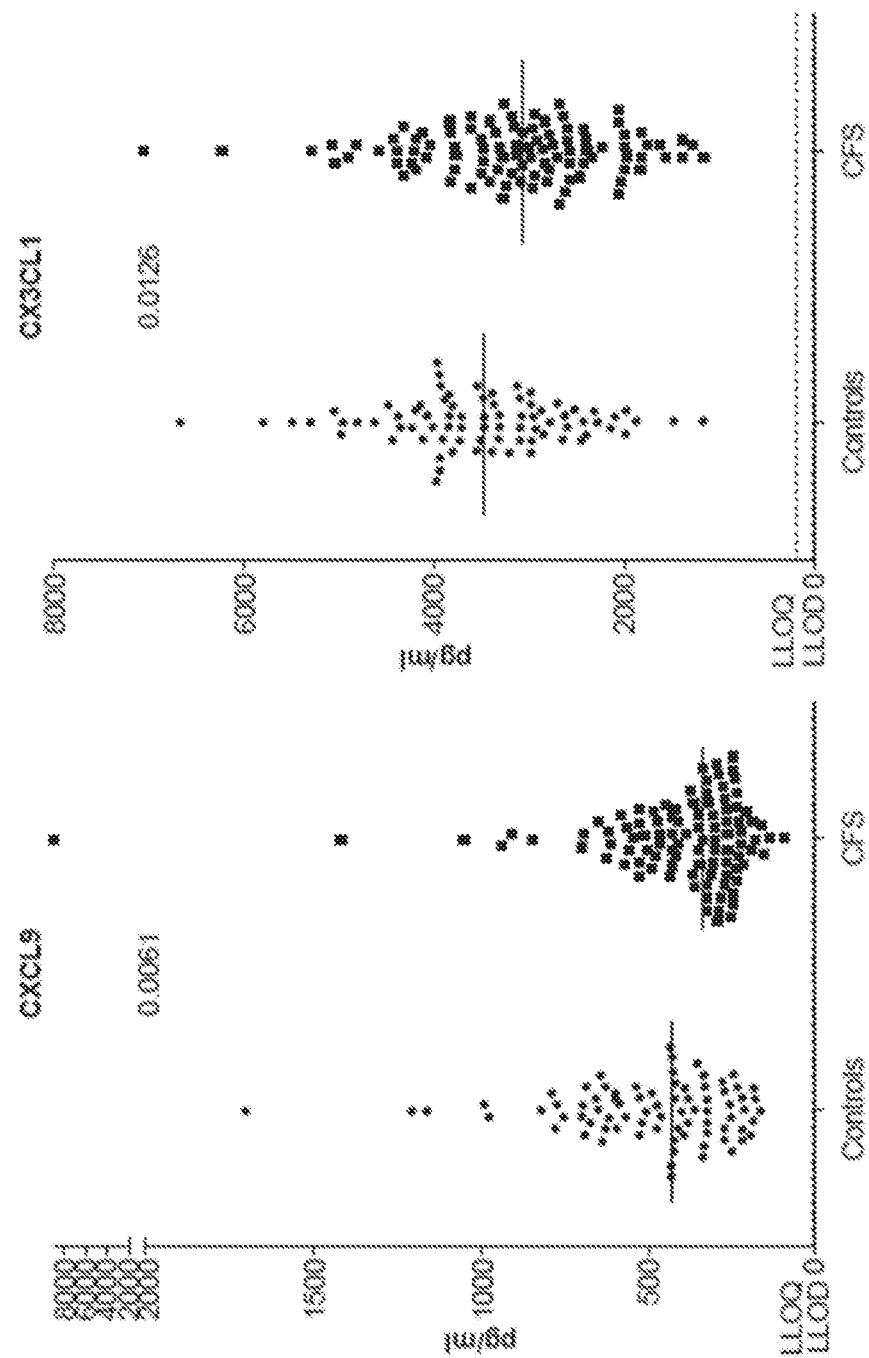
Figure 4A:
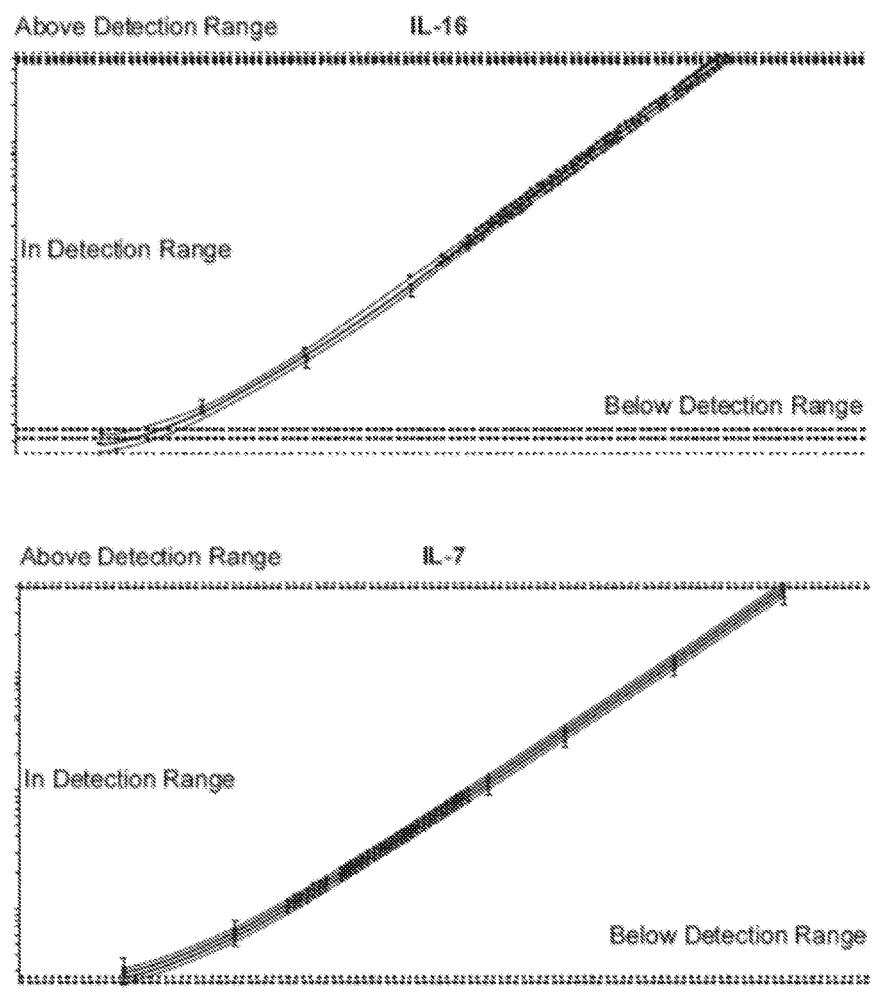
Figure 4B:
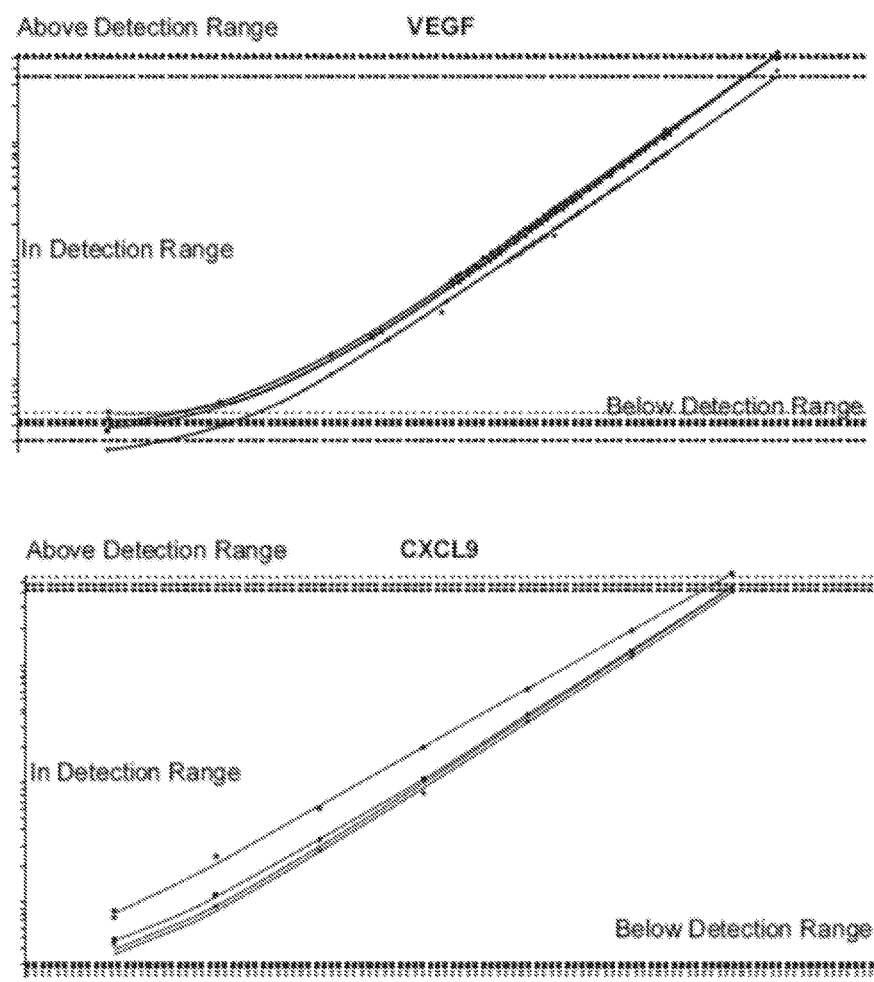

After correction for multiple comparisons, univariate hypothesis testing revealed 6 analytes that had significantly different median group values (FIG. 3). Five analytes had significantly decreased levels due to CFS/ME (IL-16, IL-7, VEGF, CXCL9, CX3CL1) and one analyte was significantly increased (CCL24). Significant changes were also observed in the levels of IL-17 and TNF-β; however, for these analytes, the majority of measured concentrations were below the LLOQ and thus unreliable. The concentrations for all other significantly altered analytes were well above the LLOD and LLOQ and the standard curves from different plates were very well overlapped, indicating minimal inter-plate variation and highly reproducible data (FIG. 4). FIG. 4 shows that the concentration of the measured analytes was in detection range and the standard curves from different plates are highly overlapped, indicative of very low inter-plate variability (see datapoints on the curves; the upper limits of detection and the lower limits of detection are depicted on the top part and bottom part of each graph). Moreover, signal analysis showed a high level of consistency between plates with very low variations consistent with minimal matrix effect in the assay. This was confirmed by a very low Inter-CV of 5% to 18% for the different measurements and the Intra-CV values were also very low, varying from 3% to 9% for different cytokines/chemokines/growth factors (FIG. 3).

Figure 5:
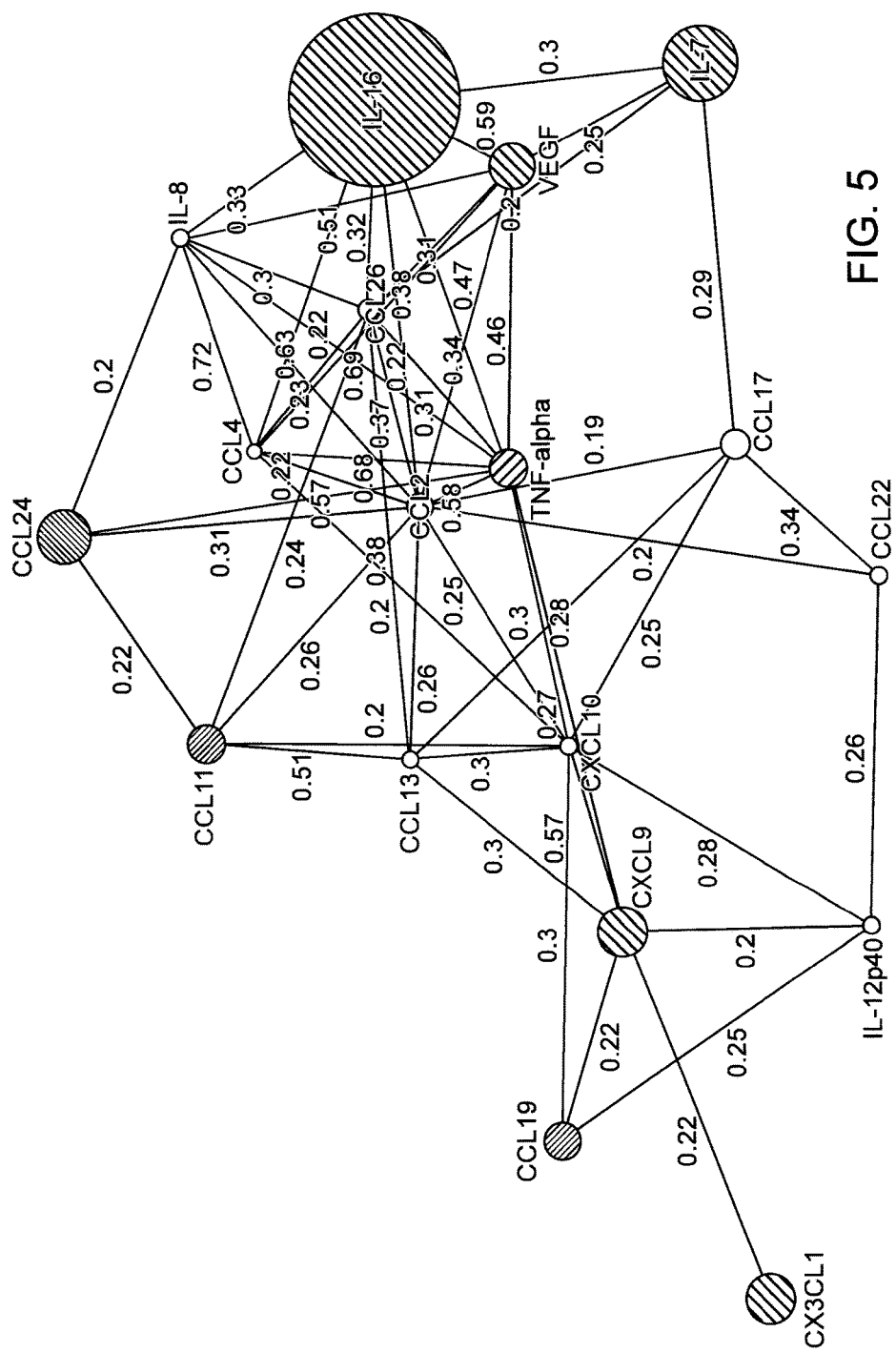
FIG. 5 provides results from correlation analysis of analytes expressed at levels above LLOD and LLOQ.

The spring-embedded correlation analysis of the 18 reliably quantified analytes showed that the significant analytes gathered into 3 clusters (FIG. 5). In particular IL-16, IL-7 and VEGF were significantly down regulated and tightly correlated. The other two clusters had less significance; a cluster including CCL24 and CCL11 and a loose cluster including CXCL9, CX3CL1, and CCL19.

Multivariate Data Analysis:

In order to identify those analytes best linked with CFS/ME disease, we used two sophisticated statistical tools to analyze our data. LASSO-LR produced an optimal model using three analytes (IL-16, IL-7, and CCL24) that resulted in the following diagnostic regression model:

$$\log it(y) = 3.98 - 1.24 \times \ln(IL\text{-}16) - 0.92 \times \ln(IL\text{-}7) + 0.89 \times \ln(CCL24)$$

Figures 6A, 6B:
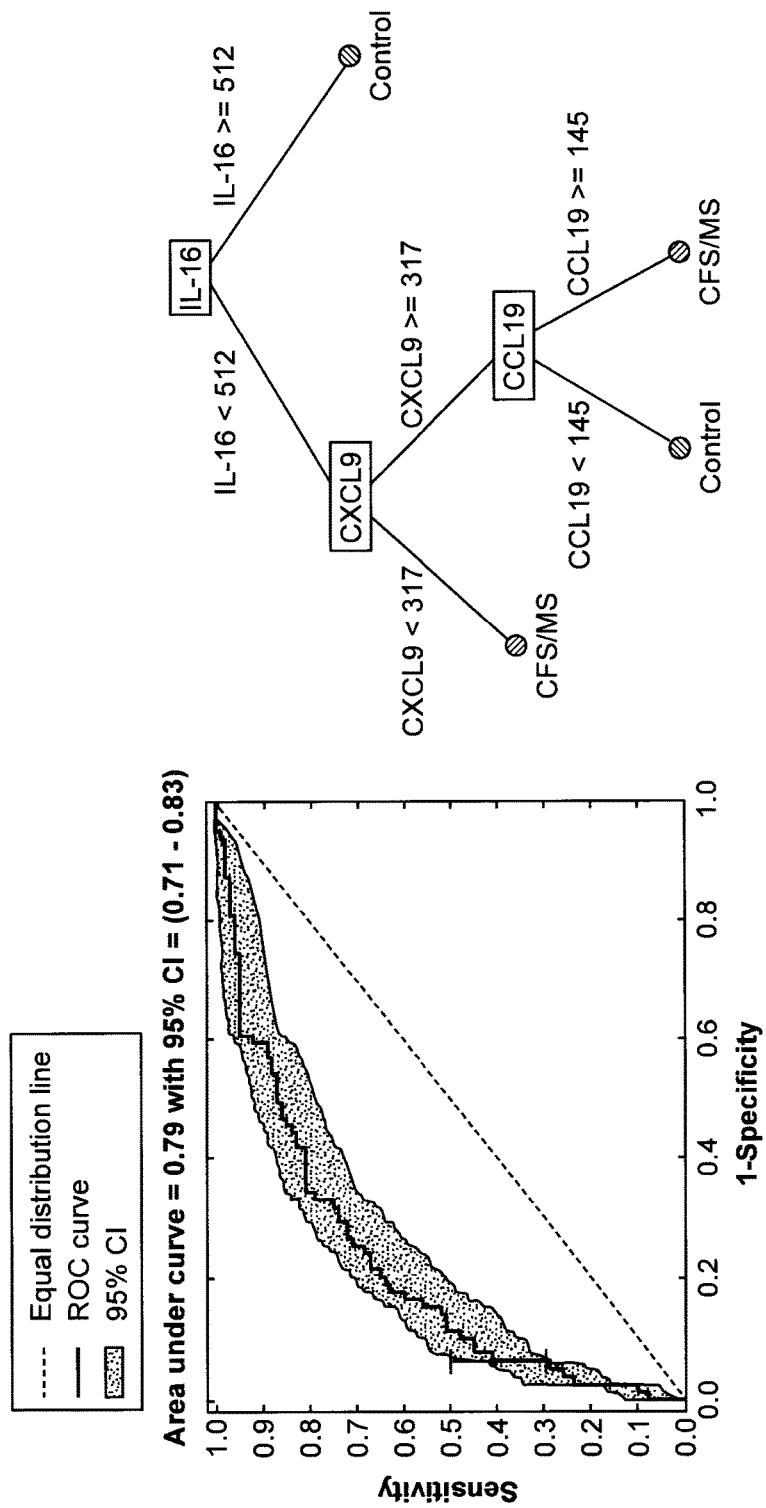
FIGS. 6A-6B depict results from multivariate data analysis.

The corresponding ROC curve had an AUC of 0.79 (95% CI: 0.71-0.83) (FIG. 6A). For a fixed specificity of 94% the corresponding sensitivity for predicting CFS/ME was 41% (95% CI: 0.29-0.49). The model statistics are described in FIG. 7. According to this specificity, if the predicted score, y, for a given individual is >0.77, the diagnosis would be CFS/ME, otherwise control.

CART produced an optimal decision tree using three analytes (IL-16, CXCL9, and CCL19) that resulted in the following diagnostic rule:

$$if \begin{cases} (IL\text{-}16 < 512 \text{ AND } CXCL9 < 317) \\ \text{OR} \\ (IL\text{-}16 < 512 \text{ AND } CXCL9 \geq 317 \text{ AND } CCL19 \geq 145) \end{cases}$$

then CFS else Control

For a fixed specificity of 96% the corresponding sensitivity for predicting CFS/ME was 43% (95% CI: 0.35-0.51). The decision tree from which the diagnostic rule was derived is shown in FIG. 6, panel b. Although the CART model had better predictive accuracy, given the size of this data set, the difference in model performance with that derived from LASSO-LR was not statistically significant.

To accommodate the complex etiological nature of CFS/ME, this study used a specifically designed multiplex ELISA assay to measure the plasma levels of thirty-four cytokines, chemokines and growth factors (several of which have not been previously measured in the context of CFS/ME), drawn from a carefully defined patient cohort. A rigorous quality assurance protocol was implemented where only the analytes in which all measurements were above the LLOQ were considered robust enough for subsequent statistical analysis (n=18). When comparing CFS/ME patients to healthy gender- and age-matched controls, a total of six analytes were altered significantly. Of these, the most significant changes were reductions in the plasma levels of IL-16 and IL-7, both of which were significantly correlated with reductions in VEGF plasma levels (FIG. 5).

The correlation analysis (FIG. 5) showed that the analytes significantly altered in CFS/ME patients clustered into three groups, each of which may reflect varying symptoms in CFS/ME subsets. The most significant cluster comprises IL-16, IL-7 and VEGF (Node color=blue). The second cluster includes CCL11 (Node color=orange) and CCL24 (Node color=Red). The third cluster includes CCL19 (Node color=orange), CXCL9 (Node color=blue), and CX3CL1 (Node color=blue).

Despite the urgent need for a serologic diagnostic for CFS/ME, no blood test that is reproducible and validated has yet been developed for CFS/ME patients. The two algorithms described herein produced very similar predictive abilities (LASSO-LR: specificity of 94% and sensitivity of 41%; CART: specificity of 96% and sensitivity of 43%) even though they are based on different subsets of the CFS/ME profile. The LASSO-LR model used analytes IL-16, IL-7, and CCL24, whereas, the CART model used analytes IL-16, CXCL9, and CCL19. When mapped onto the correlation plot (FIG. 5), the LASSO-LR model focuses on the both the IL-16/IL-7/VEGF cluster and the CCL24/CCL11 cluster, whereas the CART model focused on the IL-16/IL-7/VEGF cluster and the CCL19/CXCL9/CX3CL1 cluster. It is clear that the pivotal component of the CFS/ME biomarker profile is the IL-16.

In conclusion, our study shows significant changes in the cytokine, chemokine and growth factor profile of CFS/ME patients. Moreover, the known biological effects of these various analytes is consistent with known disease manifestations observed in CFS/ME patients. The two assay algorithms described here provide much-needed clinical diagnostic tools to help clinicians diagnose CFS/ME as well as opening up new therapeutic avenues.

TABLE 2

List of cytokines and chemokines that are referred to with alternate names:

| Name | Alternate Name |
|---|---|
| Monocyte chemotactic protein 1 (MCP-1) | CCL2 |
| Monocyte chemotactic protein-4 (MCP-4) | CCL13 |
| Macrophage inflammatory protein 1-beta (MIP-1β) | CCL4 |
| Macrophage inflammatory protein 3-beta (MIP-3β) | CCL19 |
| Interferon gamma-induced protein 10 (IP-10) | CXCL10 |
| Macrophage-derived chemokine (MDC) | CCL22 |
| Macrophage inflammatory protein 1-alpha (MIP-1α) | CCL3 |
| Thymus and activation regulated chemokine (TARC) | CCL17 |
| Fraktalkine | CX3CL1 |
| Monokine induced by gamma interferon (MIG) | CXCL9 |
| Eotaxin-1 | CCL11 |
| Eotaxin-2 | CCL24 |
| Eotaxin-3 | CCL26 |

The invention claimed is:

1. A method comprising:
   measuring a level of IL-16, a level of IL-7, and a level of VEGF in a body fluid sample of a subject suspected of having chronic fatigue syndrome/myalgic encephalomyelitis (CFS/ME), or
   measuring a level of IL-16, a level of IL-7, and a level of CCL24 in a body fluid sample of a subject suspected of having CFS/ME.

2. The method of claim 1, wherein the method comprises measuring the level of IL-16, the level of IL-7, and the level of VEGF in a body fluid sample of a subject suspected of having CFS/ME.

3. The method of claim 2, wherein the method further comprises measuring a level of CCL24 in the body fluid sample of the subject.

4. The method of claim 2, wherein the method further comprises measuring a level of CCL11 in the body fluid sample of the subject.

5. The method of claim 2, wherein the method further comprises measuring a level of CXCL9 in the body fluid sample of the subject.

6. The method of claim 2, wherein the method further comprises measuring a level of CCL19 in the body fluid sample of the subject.

7. The method of claim 2, wherein the method further comprises measuring a level of CX3CL1 in the body fluid sample of the subject.

8. The method of claim 2, wherein the method comprises measuring the level of IL-16, the level of IL-7, and the level of CCL24 in a body fluid sample of a subject suspected of having CFS/ME.

9. The method of claim 8, wherein the method further comprises measuring a level of VEGF in the body fluid sample of the subject.

10. The method of claim 8, wherein the method further comprises measuring a level of CCL11 in the body fluid sample of the subject.

11. The method of claim 8, wherein the method further comprises measuring a level of CXCL9 in the body fluid sample of the subject.

12. The method of claim 8, wherein the method further comprises measuring a level of CCL19 in the body fluid sample of the subject.

13. The method of claim 8, wherein the method further comprises measuring a level of CX3CL1 in the body fluid sample of the subject.

14. The method of claim 1, wherein measuring comprises contacting a substrate comprising antibodies that bind to IL-16 IL-7, and VEGF or CCL24 with the body fluid sample.

15. The method of claim 1, wherein the method comprises detecting the formation of an antibody-IL-16 complex, an antibody-IL-7 complex, and an antibody-VEGF complex or an antibody-CCL24 complex using a detectably labeled antibody that binds to IL-16, IL-7, and VEGF or CCL24.

16. The method of claim 1, wherein the body fluid sample is a plasma sample.

17. The method of claim 1, wherein the body fluid sample is a serum sample.

* * * * *